US008202912B2

United States Patent
Curatolo et al.

(10) Patent No.: US 8,202,912 B2
(45) Date of Patent: *Jun. 19, 2012

(54) PHARMACEUTICAL COMPOSITIONS PROVIDING ENHANCED DRUG CONCENTRATIONS

(75) Inventors: William J. Curatolo, Niantic, CT (US); Ravi M. Shanker, Groton, CT (US); Walter C. Babcock, Bend, OR (US); Dwayne T. Friesen, Bend, OR (US); James A. S. Nightingale, Band, OR (US); Douglas A. Lorenz, Bend, OR (US)

(73) Assignee: Bend Research, Inc., Bend, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/208,305

(22) Filed: Aug. 11, 2011

(65) Prior Publication Data

US 2011/0294902 A1 Dec. 1, 2011

Related U.S. Application Data

(62) Division of application No. 09/742,785, filed on Dec. 20, 2000, now Pat. No. 8,026,286.

(60) Provisional application No. 60/171,841, filed on Dec. 23, 1999.

(51) Int. Cl.
| | |
|---|---|
| A61K 47/32 | (2006.01) |
| A61K 9/14 | (2006.01) |
| A61K 9/16 | (2006.01) |
| A61K 9/22 | (2006.01) |

(52) U.S. Cl. ............... 514/772.4; 424/489; 424/486; 424/493; 424/468

(58) Field of Classification Search ............ 424/489, 424/486, 493, 468; 514/772.4
See application file for complete search history.

(56) References Cited

U.S. PATENT DOCUMENTS

| | | | | | |
|---|---|---|---|---|---|
| 5,189,148 | A | * | 2/1993 | Akiyama et al. | 530/399 |
| 5,273,753 | A | * | 12/1993 | Ishihara et al. | 424/439 |
| 6,548,555 | B1 | * | 4/2003 | Curatolo et al. | 514/772.4 |

FOREIGN PATENT DOCUMENTS

EP 0 826 685 A1 * 3/1998

* cited by examiner

*Primary Examiner* — Blessing Fubara
(74) *Attorney, Agent, or Firm* — Chernoff, Villhauer, McClung & Stenzel

(57) ABSTRACT

A drug in a solubility-improved form is combined with a concentration-enhancing polymer in a sufficient amount so that the combination provides substantially enhanced drug concentration in a use environment relative to a control comprising the same amount of the same solubility-improved form of drug without the concentration-enhancing polymer.

7 Claims, No Drawings

PHARMACEUTICAL COMPOSITIONS PROVIDING ENHANCED DRUG CONCENTRATIONS

This is a divisional of Ser. No. 09/742,785 filed Dec. 20, 2000, now U.S. Pat. No. 8,026,286 which is a non-provisional of Ser. No. 60/171,841 filed Dec. 23, 1999 and, pursuant to 35 USC 120, priority of both those applications is claimed.

BACKGROUND OF THE INVENTION

The invention relates to compositions comprising a combination of a drug and a concentration-enhancing polymer that enhances the concentration of the drug in a use environment relative to control compositions that are free from the concentration-enhancing polymer.

Low-solubility drugs often show poor bioavailability or irregular absorption, the degree of irregularity being affected by factors such as dose level, fed state of the patient, and form of the drug. Increasing the bioavailability of low-solubility drugs has been the subject of much research. Increasing bioavailability hinges on improving the concentration of the drug in solution to improve absorption.

It is known that many low-solubility drugs can be formulated so as to increase the maximum concentration of the drug that will dissolve in an aqueous solution in in vitro tests. When such a drug in a solubility-improved form is initially dissolved in an environment of use, such as in gastric fluid, the solubility-improved form of the drug initially provides a higher concentration of dissolved drug in the environment of use relative to other forms of the drug and relative to the equilibrium concentration of the drug. In addition, it has been shown that when such forms are tested in vivo they can enhance the relative bioavailability of the drug, presumably by enhancing, at least temporarily, the concentration of dissolved drug present in the gastrointestinal (GI) tract. However, as discussed below, the higher concentration obtained is often only temporary, with the solubility-improved drug form quickly converting to the low-solubility form after delivery to a use environment.

For example, it is known that some low-solubility drugs may be formulated in highly soluble salt forms that provide temporary improvements in the concentration of the drug in a use environment relative to another salt form of the drug. An example of such a drug is sertraline, which in the lactate salt form has a higher aqueous solubility at pH 3 than the HCl salt form. However, when a high-solubility salt form such as sertraline lactate is dosed to an aqueous solution (either in vitro or in vivo) that has both high levels of chloride present as well as buffers to control the pH, the enhanced solubility of the sertraline lactate is either short lived or not achieved at all since the sertraline can quickly convert to crystalline or amorphous HCl or free base forms that have lower solubility than sertraline lactate.

Another drug form known to provide, at least temporarily, increased concentrations in solution of low-solubility drugs consists of drug in a hydrate or solvate crystalline form of the drug. Such forms often have higher aqueous solubility relative to the lowest solubility crystalline form and, therefore, provide higher concentrations of drug.

It is known that some drugs are capable of forming more than one crystal structure, despite having identical chemical compositions. (This is in contrast to salt forms, solvates, or hydrates that have varying chemical compositions.) These various crystal structures are often referred to as polymorphs. Polymorphs comprise another drug form that temporarily provides increased concentrations in solution. Some polymorphs, also referred to herein as "high-energy crystalline forms," have higher aqueous solubility and therefore can provide enhanced aqueous concentration of the drug relative to other crystal structures and relative to the equilibrium concentration.

It is also well known that the amorphous form of a low-solubility drug that is capable of existing in either the crystalline or amorphous form may also temporarily provide a greater aqueous concentration of drug relative to the equilibrium concentration of drug in a use environment. It is believed that the amorphous form of the drug dissolves more rapidly than the crystalline form, often dissolving faster than the drug can precipitate from solution. As a result, the amorphous form may temporarily provide a greater-than equilibrium concentration of drug.

Another method that can temporarily provide a greater than equilibrium drug concentration is to include a solubilizing agent in the drug form. Such solubilizing agents promote the aqueous solubility of the drug. An example of the use of a solubilizing agent with a drug to increase aqueous solubility is the use of solubilizing agents with sertraline. As disclosed in commonly assigned PCT Application No. 99/01120, now abandoned, when sertraline is codissolved in aqueous solution with a solubilizing agent, for example, citric acid, the solubility of sertraline is dramatically increased. As mentioned above, when sertraline HCl is dosed along with citric acid to a chloride-containing buffer solution or the GI tract, the maximum sertraline concentration achieved can exceed the solubility of sertraline HCl. This concentration enhancement is thought to be partly due to a locally lower pH in the use environment due to the presence of the citric acid and partly due to the presence of citrate counter ions, as sertraline citrate is more soluble than sertraline chloride. However, the enhanced concentration is typically short-lived as sertraline quickly converts to a low-solubility form which could be, depending on the use environment, the solid crystalline or amorphous HCl salt and/or crystalline or amorphous free base.

Yet another technique for temporarily achieving a greater than equilibrium concentration of drug in a use environment is to formulate the drug as an aqueous or organic solution. For example, drug can be dissolved in polyethylene glycol (PEG) or an aqueous solution of PEG to which an acid or base may be added or the drug may be dissolved in an aqueous solution of an acid or base. Alternatively, the drug can be dissolved in a pharmaceutically acceptable organic liquid such as glycerol, mono-, di-, or triglycerides, fats or oils.

While these solubility-improved drug forms show initially enhanced concentration of the drug in a use environment, nevertheless the improved concentration is often short-lived. Typically, the initially enhanced drug concentration is only temporary and quickly returns to the lower equilibrium concentration. For example, while a particular salt form of a basic drug may show improved initial aqueous concentration, the drug often rapidly converts in gastric fluid to another salt form (typically the HCl salt form) that has a much lower equilibrium concentration. In other cases, the drug maintains acceptable solubility in the low pH gastric solution, but precipitates typically as the free-base form of the drug upon passing into the small intestine where the pH is high, typically from 4.4 to 7.5. Since drug absorption occurs primarily in the intestines, such drug dosage forms that do not sustain high concentration of the drug in an intestinal solution typically yield only minor improvements in bioavailability. Likewise, a high-solubility salt form of an acidic drug can rapidly convert to another salt form that has a much lower equilibrium concentration. Similar effects are observed even for high solubility salt forms of zwitterionic drugs. Similarly, once the high-energy crystalline form of a drug (e.g., a polymorph) dissolves, the drug often rapidly precipitates or crystallizes from solution as it changes to a lower energy crystalline form or an amorphous form with lower solubility which causes concentration of dissolved drug to approach a lower equilibrium concentration.

One approach to increase the bioavailability of low-solubility drugs has involved forming amorphous dispersions of drugs with polymers. Examples of attempts to increase drug concentration by forming a dispersion of the drug with a polymer include Lahr et al., U.S. Pat. No. 5,368,864, Kanikanti et al., U.S. Pat. No. 5,707,655, and Nakamichi et al., U.S. Pat. No. 5,456,923.

However, creating an amorphous dispersion of a drug and polymer(s) does have some drawbacks. There is a risk that in the process of creating the dispersion, the drug will be altered. For example, some drugs may degrade at the elevated temperatures used to form some dispersions. Some processes use organic solvents which must be thoroughly removed to avoid drug degradation. Solvents must be chosen which dissolve both the drug and the polymer. The process of forming such dispersions is also time-consuming and expensive. In addition, the dispersions may in some cases be unstable and may either chemically degrade over time at moderate temperature and humidity levels or the drug may convert to a lower energy and lower solubility amorphous or crystalline form.

Increasing drug solubilization by using combinations of drug and polymer has also been described. For example, Martin et al., U.S. Pat. No. 4,344,934 mixed poorly-soluble drugs with polymers such as hydroxypropyl methyl cellulose (HPMC) and added an aqueous surfactant solution to the drug-polymer mixture. While this results in improved dissolution, there is only slight enhancement of drug concentration relative to the equilibrium concentration. Piergiorgio et al., U.S. Pat. No. 4,880,623 used solvent processing to co-precipitate nifedipine with PEG and adsorbed this onto polymers such as HPMC, or onto other excipients. While increased drug bioavailability was observed, no comparison was made between different drug forms. Uedo et al., U.S. Pat. No. 5,093,372 mixed the sparingly-soluble drug exifone with polymers such as HPMC to increase bioavailability. However, this did not result in any enhanced drug concentration of the drug/polymer mixture relative to the bulk crystalline form of the drug.

In addition, combining drugs with solubilizing polymers is not universally available to improve bioavailability for all low-solubility drugs. Drug solubilization is usually highly dependent upon the chemical structure and physical properties of the specific drug and therefore the particular polymer, if any, that may prove to solubilize the drug varies from drug to drug. It is often difficult and time-consuming to select polymers which achieve improved solubilization, since the drug-polymer interaction is poorly understood. Often, addition of polymers simply speeds dissolution of the drug, as opposed to providing enhanced concentration.

Usui, et al., *Inhibitory Effects of Water-soluble Polymers on Precipitation of RS-8359*, Int'l J. of Pharmaceutics 154 (1997) 59-66, discloses the use of three polymers, namely hydroxy propyl methyl cellulose, hydroxy propyl cellulose, and polyvinylpyrrolidone to inhibit precipitation of the low-solubility drug RS-8359. The drug and polymer were dissolved in a mixture of 0.5 N HCl and methanol, and then added to a phosphate buffer solution. Usui et al. observed that the particular polymers inhibited crystallization of the drug.

Accordingly, what is still needed is a composition comprising a drug that provides enhanced concentration of the drug in aqueous solution relative to the equilibrium concentration of the drug, that maintains the concentration of the drug in such a solution over time or at least reduces the rate at which the drug concentration decreases from the enhanced concentration to the equilibrium concentration, that may be prepared using processes that will not alter or degrade the drug, that may be prepared without relying on solvent processing, that is stable under typical storage conditions, that may be easily and cheaply prepared and that ultimately enhances the bioavailability of poorly soluble drugs. These needs and others that will become apparent to one of ordinary skill are met by the present invention, which is summarized and described in detail below.

BRIEF SUMMARY OF THE INVENTION

The present invention overcomes the drawbacks of the prior art by providing a composition comprising (1) a drug in a solubility-improved form and (2) a concentration-enhancing polymer.

In a first aspect of the invention, the concentration-enhancing polymer is combined with the drug form in a sufficient amount so that the composition provides a maximum concentration of the drug in a use environment that is at least 1.25-fold that of an equilibrium concentration of the drug in the use environment without the polymer present. The composition also provides a concentration of the drug in the use environment that exceeds the equilibrium concentration for a longer time than does a control composition that comprises an equivalent quantity of the drug in the solubility-improved form which is free from the concentration-enhancing polymer.

In a second aspect of the invention, the concentration-enhancing polymer is present in a sufficient amount so that the composition provides a dissolution area under the concentration-versus-time curve (AUC) for a period of at least 90 minutes during the 1200 minutes immediately following introduction to the use environment that is at least 1.25-fold that of the corresponding area under the curve provided by the same control composition mentioned above.

In a third aspect of the invention, the concentration-enhancing polymer is present in a sufficient amount so that the composition provides a relative bioavailability that is at least 1.25.

In a fourth aspect of the invention, a method is provided for co-administering to a patient in need of a drug (1) the drug in a solubility-improved form and (2) a concentration-enhancing polymer. The concentration-enhancing polymer is co-administered in a sufficient amount so that there is provided in the use environment of the patient a maximum concentration of the drug that is at least 1.25-fold that of the equilibrium concentration of the drug in the use environment of the patient without the polymer present. The method also provides a concentration of the drug in the use environment of the patient that exceeds the equilibrium concentration for a longer time than does the control composition mentioned above.

In a fifth aspect of the invention, a method is provided for co-administering to a patient in need of a drug (1) the drug in a solubility-improved form and (2) a concentration-enhancing polymer. The concentration-enhancing polymer is co-administered in a sufficient amount so that there is provided in the use environment of the patient a dissolution area under the concentration-versus-time curve for a period of at least 90 minutes, during the 1200 minutes immediately following introduction to the use environment of the patient, that is at least 1.25-fold the corresponding area under the curve provided by the same control composition mentioned above.

In a sixth aspect of the invention, a method is provided for co-administering to a patient in need of a drug (1) the drug in a solubility-improved form, and (2) a concentration-enhancing polymer. The concentration-enhancing polymer is co-administered in a sufficient amount so that there is provided a relative bioavailability at least 1.25-fold.

The term "solubility-improved form" as employed herein refers to a form of the drug which has increased solubility relative to the least soluble form of the drug known. Thus, the term implies that a less soluble form of the drug exists and is either known or has been determined, i.e., known, for example, from the scientific or patent literature, or determined by or otherwise known to the investigator. A "solubility-improved form" may consist of a highly soluble form of the drug alone, may be a composition comprising a highly soluble form of the drug plus inert excipients, or may be a composition comprising the drug in a poorly or highly soluble form and one or more excipients which have the effect of increasing the solubility of the drug, regardless of the length of time for which the solubility is increased. Examples of "solubility-improved forms" include but are not limited to: (1) a crystalline highly soluble form of the drug such as a salt; (2) a high-energy crystalline form of the drug; (3) a hydrate or solvate crystalline form of a drug; (4) an amorphous form of a drug (for a drug that may exist as either amorphous or crystalline); (5) a mixture of the drug (amorphous or crystalline) and a solubilizing agent; or (6) a solution of the drug dissolved in an aqueous or organic liquid.

Alternatively, the term "solubility-improved form" refers to a form of the drug alone or in a composition as is described above that, when delivered to an in vivo environment of use (such as, for example, the gastrointestinal tract of a mammal) or a physiologically relevant in vitro solution (such as phosphate buffered saline or a Model Fasted Duodenal solution described below) provides, or is capable of providing, at least temporarily, a concentration of drug that is at least 1.25-fold the equilibrium concentration of drug in the use environment. (As used here, the term "equilibrium concentration" is defined below.)

A solubility-improved form of a drug is one that meets at least one of the above definitions.

Since the crystalline free base and crystalline hydrochloride forms of a basic drug generally have relatively low solubility relative to other drug forms and because solubilized drug generally precipitates from the use environment of the GI tract of an animal as one of these crystalline forms (or their amorphous counterparts), a preferred solubility-improved form of a basic drug is a form of the drug that has an aqueous solubility at least 2-fold the solubility of the more soluble of the crystalline hydrochloride salt and the crystalline free base drug form.

In a preferred embodiment of the invention, the concentration-enhancing polymer has a hydrophobic portion and a hydrophilic portion. In a most preferred embodiment, the concentration-enhancing polymer is an ionizable polymer that is soluble in a use environment when significantly ionized at physiologically relevant pHs.

The solid compositions of the present invention are generally combinations comprising the solubility-improved form and concentration-enhancing polymer. "Combination" as used herein means that the solubility-improved form and concentration-enhancing polymer may be in physical contact with each other or in close proximity but without the necessity of being physically mixed. For example, the solid composition may be in the form of a multi-layer tablet, as known in the art, wherein one or more layers comprises the solubility-improved form and one or more different layers comprises the concentration-enhancing polymer. Yet another example may constitute a coated tablet wherein either the solubility-improved form of the drug or the concentration-enhancing polymer or both may be present in the tablet core and the coating may comprise the solubility-improved form or the concentration-enhancing polymer or both. Alternatively, the combination can be in the form of a simple dry physical mixture wherein both the solubility-improved form and concentration-enhancing polymer are mixed in particulate form and wherein the particles of each, regardless of size, retain the same individual physical properties that they exhibit in bulk. Any conventional method used to mix the polymer and drug together such as physical mixing and dry or wet granulation, which does not substantially convert the drug and polymer to a molecular dispersion, may be used.

Alternatively, the drug and concentration-enhancing polymer may be co-administered to a patient in need of the drug. The drug and concentration-enhancing polymer may be administered in separate or the same dosage forms, and may also be administered at essentially the same time or at different times.

However, compositions comprising dispersions, particularly molecular dispersions wherein the dispersion is formed prior to delivery to the use environment, of drug and polymer as disclosed in the art discussed above, form no part of this invention and are excluded therefrom. In general, a molecular dispersion of drug and polymer is one in which the physical properties of the mixture, such as melting point or glass-transition temperature, are transformed from those characteristic of the bulk (i.e. undispersed) polymer and drug. In the compositions of the present invention, as disclosed above, the drug and polymer each retain their individual respective physical properties, such as melting point and/or glass-transition temperature. Thus, solid compositions made by dissolving a drug plus the concentration-enhancing polymer in a solvent followed by drying from the solvent, or by co-grinding, or by extruding with heating, or by precipitation by mixing a solution of the polymer and a solution of the drug such that a dispersion of polymer and drug precipitates, or by other methods such that a molecular dispersion of drug and concentration-enhancing polymer is formed do not form a part of this invention.

Also not a part of this invention is the special case where a basic drug with high gastric (pH 1 to 2) solubility and low intestinal solubility (pH 6 to 8) is dosed as its lowest-solubility form with a concentration-enhancing polymer. In such cases, a high drug concentration is achieved as a result of the effect of the naturally occurring acidic environment of the stomach rather than as a result of utilizing a solubility-improved form of the drug. Since the key inventive component of this invention is combining a solubility-improved drug form with a concentration-enhancing polymer, cases in which a high drug solubility is achieved solely as a result of the natural environment of the stomach does not constitute a part of this invention.

The various aspects of the present invention have one or more of the following advantages.

The solubility-improved form of the drug when dissolved in the use environment provides an initial concentration of drug that exceeds the equilibrium concentration of drug, while the concentration-enhancing polymer retards the rate at which the initially enhanced drug concentration falls to the equilibrium concentration. The result is that the compositions of the present invention provide an improved dissolution area-under-the-curve ("AUC") that is greater than that provided by the drug alone. While not required to be within the scope of the present invention, in some aspects, the solubility-improved form provides a maximum drug concentration that exceeds the maximum drug concentration achieved by the drug alone. Nevertheless, the advantages of the invention may be obtained by merely retarding the rate at which the enhanced drug concentration falls to the equilibrium concentration, even without increasing the maximum drug concentration relative to the drug alone.

In any event, improving the AUC means that the compositions of the present invention may also provide enhanced bioavailability of the drug by increasing the concentration of drug which remains dissolved in the use environment, particularly in the GI tract. Improving the concentration of the drug in solution allows higher blood levels to be achieved, in some cases enabling an effective level to be reached or in other cases, allowing effective blood levels to be reached at lower drug dosage levels, which in turn decreases the amount of drug that must be dosed, reduces the blood level variability, and also decreases the size of the dosage form depending on the amount of polymer needed. Accordingly, the compositions of the present invention enable the effective use of drugs having low aqueous solubility which otherwise do not have a sufficiently high bioavailability, to be effective, and also enhance bioavailability to reduce the required dose.

Furthermore, because the compositions of the present invention provide for a higher concentration in the use environment, and because once a high drug concentration is achieved the concentration tends to remain high due to inhibition of precipitation or crystallization of the drug, they reduce the adverse effects of chemical species present in the use environment such as chloride or hydrogen ions or bile salts on the absorption of drug. Thus, in cases where the use environment is the GI tract, the compositions of the present invention will show less variability on the fed/fast state of the human or animal.

In addition, for those forms in which the drug is present in a crystalline state, the drug is less likely to have its physical or chemical state altered by, for example, various degradation reactions, and in turn, its pharmaceutical characteristics altered during preparation of the dosage form or during storage relative to, for example, a solid amorphous dispersion of the drug which can undergo degradation or crystallization upon storage. In addition, because the compositions containing crystalline drug are simple physical mixtures (as opposed to dispersions), the compositions do not suffer the storage stability problems of many dispersions. The compositions, being in the nature of solid mixtures, or simple solutions, are also easily prepared using conventional mixing techniques.

The foregoing and other objectives, features, and advantages of the invention will be more readily understood upon consideration of the following detailed description of the invention.

DETAILED DESCRIPTION OF THE PREFERRED EMBODIMENTS

The present invention provides a composition comprising a drug in a solubility-improved form and a concentration-enhancing polymer. The solubility-improved form may be a crystalline highly soluble salt form of the drug, a high-energy crystalline form of the drug (e.g., a high-solubility polymorph), a hydrate or solvate crystalline form of the drug, an amorphous form of the drug, a mixture of the drug with a solubilizing agent, or a solution of the drug in an aqueous or organic liquid. Suitable drug(s) and suitable concentration-enhancing polymer(s) are discussed in detail below.

Solid drug in the solubility-improved form and concentration-enhancing polymer are termed "simple physical mixtures" when they are combined using conventional mixing techniques such as combining and physically stirring dry components together or mixing by dry- or wet-granulating. Thus, a simple physical mixture of drug and polymer means that in the mixture, the drug has properties, such as melting point in the case of crystalline drug, or glass-transition temperature in the case of amorphous drug, that match those properties of the drug alone. This contrasts with a drug/polymer molecular dispersion for which no drug melting point is observed and a glass-transition temperature is observed that differs from the polymer and drug alone and varies as a function of the drug/polymer mass ratio in the dispersion.

The drug in the solubility-improved form and the concentration-enhancing polymer can also be combined via co-administration of the two components to a use environment. By co-administration is meant that the solubility-improved drug form is administered separately from, but within the same general time frame, as the concentration-enhancing polymer. For example, the solubility-improved drug form can be administered in its own dosage form that is taken at approximately the same time as the concentration-enhancing polymer, which is in a separate dosage form. The time difference between administration of the drug in the solubility-improved form and the concentration-enhancing polymer is such that they come into physical contact in the use environment. When they are not co-administered at the same time it is generally preferable to administer the concentration-enhancing polymer prior to administration of the drug in the solubility-improved form.

It is known that many drugs are capable of existing in several forms and may be formulated in a solubility-improved form to provide an initially enhanced aqueous concentration of the drug relative to the equilibrium concentration of the lowest-solubility form of the drug. However, in the absence of the concentration-enhancing polymer, the initially enhanced drug concentration can often quickly decrease to approximately the equilibrium concentration of the drug as the drug precipitates or crystallizes from solution. This may occur through a variety of mechanisms. For example, a highly soluble salt form may, due to the presence of other ions in the use environment, convert to another salt form having a lower equilibrium concentration. Dissolved drug may also change its ionic state, for example, by protonation or de-protonation, resulting in precipitation or crystallization from solution as a lower solubility form. Alternatively, a high-energy crystalline form upon dissolution may rapidly convert to the low-energy crystalline form, which has a lower equilibrium concentration. Likewise, the drug may be mixed with a solubilizing agent. For example, particularly when the drug is a base, the drug may have higher aqueous solubility at low pH. Such a drug may be mixed with a solubilizer such as an inorganic or organic acid. The acid may serve as a solubilizing agent by lowering the pH within the dosage form as well as that of the use environment near the dosage form, thus increasing the local solubility of the drug. However, as the drug diffuses away from the dosage form, the pH of the use environment can increase due to the lower concentration of the solubilizing acid, thus decreasing drug solubility and resulting in precipitation of the drug. Thus, such solubility-improved drug forms, by themselves, generally have limited success in producing the desired increase in bioavailability. In some cases, precipitation or crystallization as a low-solubility form is so fast that the maximum solubility of the solubility-improved form is not even reached.

The key to the present invention was the recognition by the inventors that the initially enhanced concentration of the drug in solution provided by a drug in a solubility-improved form could be maintained, and in some cases enhanced, by retarding precipitation, crystallization, or conversion of the drug to lower solubility forms through the use of a concentration-enhancing polymer. Thus, without implying any particular mechanism of action, it is believed that the concentration-enhancing polymers of this invention may be viewed as acting as crystallization or precipitation inhibitors. Surprisingly, this may be accomplished by simply combining the concentration-enhancing polymer with the drug when the drug is in a solid form, in contrast to forming a dispersion of the drug and polymer. Alternatively, the polymer can be coated onto drug-containing tablets or beads or even administered separately but to the same use environment as the solubility-improved drug form and still function to maintain for a substantial time period a greater than equilibrium drug concentration and, in turn, a higher bioavailability. In addition, when the drug is in the form of a solution in a liquid, the polymer may be co-dissolved with the drug in the liquid, be suspended in the liquid, or even comprise a capsule wall or coating that contains the liquid.

Since a drug can often exist in any of many solid crystalline or amorphous foams and because interconversion between these forms is often unpredictable, it may require a very short to a very long time for the dissolved drug concentration to reach its equilibrium value in an aqueous solution. In any case, the presence of the concentration-enhancing polymer increases the time required for the drug concentration to fall to equilibrium. In fact, when compositions of the invention are dosed to a use environment such as the GI tract where dissolved drug is absorbed from the GI fluids, much or all of the drug may be absorbed prior to the drug being substantially converted to its lowest solubility form. Typical enhancements of dissolved drug concentration over equilibrium drug concentration are on the order of 1.25-fold to 20-fold, and in some cases 20-fold to 100-fold. For example, where the control provides an equilibrium concentration of 1 mg/mL and the composition provides a maximum drug concentration of 1.25 mg/mL, the composition provides a 1.25-fold enhancement.

While not wishing to be bound by a particular theory, it is believed that the concentration-enhancing polymer(s) of the present invention generally do not have the capacity to greatly solubilize insoluble drugs (that is, to increase the equilibrium solubility of free drug). Instead, it is believed the concentration-enhancing polymers primarily act to slow the rate of precipitation or crystallization of the drug after the drug is initially dissolved. The presence of the concentration-enhancing polymer(s) thus allows the initially increased or enhanced concentration provided by the solubility-improved form of the drug to be at least partially maintained for at least a few minutes and, in some cases, for many hours. In addition, in cases where dissolution of the solubility-improved form of the drug is slow and precipitation of the low-solubility drug form, in the absence of the concentration-enhancing polymer, is fast, the presence of the concentration-enhancing polymer may result in the maximum concentration of drug observed being substantially higher than that observed in the absence of the polymer.

One possible mechanism for improving the drug concentration involves the association of the concentration-enhancing polymer and dissolved drug to form "polymer/drug assemblies." Such assemblies may constitute various forms, including polymeric micelles, high-energy polymer-drug aggregates ranging in size from a few nanometers to 1000 nanometers, polymer-stabilized drug colloids or polymer/drug complexes. An alternative view is that as dissolved drug begins to precipitate or crystallize from solution (e.g., as nucleation begins) the polymer adsorbs to these drug aggregates or nuclei, preventing, or at least retarding, the nucleation or crystal-growth process. In any case, the presence of the polymer serves to enhance the amount of drug that is dissolved or at least available for absorption. Drug present in the various drug/polymer assemblies listed above is apparently quite labile and may contribute to the drug absorption process.

The concentration-enhancing polymers of the present invention provide enhanced concentration of the drug in a use environment exceeding the equilibrium concentration for a longer period of time than a control composition comprising an equivalent quantity of drug in the solubility-improved form when subjected to a dissolution test. That is, even though the control composition may provide an enhanced concentration of drug in the use environment that exceeds the equilibrium concentration, the control does so for a shorter period of time than the compositions of the present invention which contain a concentration-enhancing polymer. Preferably, the compositions of the present invention provide enhanced drug concentration that exceed the equilibrium concentration provided by a control composition for a period of at least 15 minutes, preferably a period of at least 60 minutes, and more preferably a period of at least 90 minutes longer than does the drug concentration provided by a control composition that does not contain the concentration-enhancing polymer.

As used herein, the term "concentration of drug" in solution or in a use environment refers to drug that may be dissolved in the form of solvated monomeric molecules, so called "free drug," or any other drug-containing submicron structure, assembly, aggregate, colloid, or micelle. As used herein, a "use environment" can be either the in vivo environment of the GI tract, subcutaneous spaces, vaginal tract, arterial and venous blood vessels, pulmonary tract or intramuscular tissue of an animal, such as a mammal and particularly a human, or the in vitro environment of a test solution, such as phosphate buffered saline (PBS) or a Model Fasted Duodenal (MFD) solution. An appropriate PBS solution is an aqueous solution comprising 20 mM sodium phosphate, 47 mM potassium phosphate, 87 mM NaCl and 0.2 mM KCl, adjusted to pH 6.5. An appropriate MFD solution is the same PBS solution wherein additionally is present 7.3 mM sodium taurocholic acid and 1.4 mM of 1-palmitoyl-2-oleyl-sn-glycero-3-phosphocholine.

The inventors have found, in some cases, strong evidence for the existence of drug in the form of polymer/drug aggregates when compositions of the invention are dissolved in a use environment. In particular, it has been found that when drug, in a solubility-improved form, is dissolved in a use environment at a level that exceeds its equilibrium solubility value along with concentration-enhancing polymer, that there is a large increase in the light scattered by the solution. Dynamic light-scattering measurements show that when only polymer (such as HMPCAS or CAP) is dissolved that there are a small number of polymer aggregates in the 10 nm to 20 nm average size range. As drug is added to such solutions, there is generally little change in the light-scattering signal until the total concentration of drug exceeds the equilibrium solubility of the drug. At these higher drug levels, the lighter-scattering signal increases dramatically and dynamic light-scattering analysis shows that the average size of particles in solution have a much larger size, typically 50 nm to 1,000 nm, and in some cases from as small as 10 and up to 2,000 nm.

NMR analysis of such solutions (formed by compositions of the invention) as well as chemical analysis of any undissolved precipitate, show that the particles giving rise to this light-scattering signal are composed of polymer and drug.

Although the composition of these polymer/drug aggregates varies with the specific identity of the drug and concentration-enhancing polymer as well as their amounts, the polymer/drug aggregates generally contain from about 5 wt % to about 90 wt % polymer, the remainder comprising non-crystalline drug. In addition, the polymer/drug aggregates may also contain substantial amounts of water. Once the proper conditions are present, polymer/drug aggregates generally form rapidly, within a few minutes and are quite stable, often changing in amount and size by only 20% to 50% or less over a 1- to 20-hour period, a physiologically relevant time frame.

In addition, NMR analysis of such solutions formed by dissolution of the compositions of this invention in a use environment have been shown to have "free drug" concentrations that exceed the crystalline drug solubility by 1.5 fold to 10 fold or more and that exceed even the amorphous drug solubility. Such "supersaturated" drug concentrations may be maintained for one hour up to 20 hours or longer, more than a sufficient time to result in an increase in drug absorption rates and the total amount of drug absorbed from the GI tract.

A composition of the invention can be tested in vivo or, more conveniently, in vitro to ascertain whether it is within the scope of the invention. A composition can be dissolution-tested by adding it to a PBS or an MFD solution and agitating to promote dissolution. A composition or a method for administration of drug that meets at least one or more of the concentration criteria in either PBS or MFD or meets one or more of the concentration or bioavailability criteria when dosed orally to the GI tract of an animal, including a mammal such as a human, is a composition or method of this invention.

In one aspect, the compositions of the present invention comprising a drug in a solubility-improved form combined with a concentration-enhancing polymer provide a maximum concentration of the drug in a use environment that is at least 1.25-fold the equilibrium concentration of drug in the use environment provided by a control composition without polymer present. In addition, the drug concentration provided by the composition exceeds the equilibrium concentration for a longer period of time than does the drug concentration provided by a conventional control composition. The conventional or control composition is the drug in the solubility-improved form alone or combined with a weight of inert diluent equivalent to the weight of concentration-enhancing polymer in the inventive composition. Preferably, the maximum concentration of drug achieved with the composition of the present invention is at least 2-fold and more preferably at least 3-fold the equilibrium concentration provided by the control.

In scientific terms, the equilibrium concentration of drug is obtained when the concentration of drug in solution does not change with time. At this point, the drug has converted to its lowest energy form that is accessible from its specific environment. This form is typically the lowest solubility crystalline form of the drug. In some cases, the rate of formation of the lowest energy, lowest solubility form of the drug from in vitro or in vivo solutions can be exceedingly slow, requiring days or months. Since the residence time of an orally dosed drug in the GI tract is typically only on the order of 24 hours, for purposes of the present invention the equilibrium concentration of drug may be designated as the drug concentration at 20 hours after delivery to a use environment. Thus, as used herein and in the claims, "equilibrium concentration" means the drug concentration provided by a control composition in in vitro dissolution experiments (such as PBS or MFD solutions) after 20 hours, or the drug concentration provided by a control composition as measured using in vivo experiments after 20 hours, where a sufficient amount of drug is in the control so that a maximum theoretical drug concentration provided by the control is greater than the solubility of the drug. While in some cases the drug concentration may still be changing after 20 hours, nevertheless a comparison of performance of compositions of the present invention relative to an "equilibrium concentration" provided by a control composition measured after 20 hours in a use environment allows a determination of whether compositions are within the scope of the invention.

Alternatively, the compositions of the present invention provide a dissolution AUC for a period of at least 90 minutes during the 1200 minutes immediately following introduction to the use environment that is 1.25-fold that of a dissolution AUC provided by a control composition comprising an equivalent quantity of drug in the solubility-improved form but not containing the concentration-enhancing polymer. Dissolution AUC is the integration of a plot of the drug concentration versus time over a specified time period. For purposes of determining whether a composition or method is part of this invention, the dissolution AUC is calculated over a time period as short as 90 minutes up to a time period as long as 1200 minutes. The time period may be chosen for any time period between the time of introduction into the use environment (time=0) and 1200 minutes following introduction into the use environment. Thus, acceptable time periods include, for example, (1) from the time of introduction into the use environment to 90 minutes following introduction into the use environment; (2) from the time of introduction into the use environment to 180 minutes following introduction into the use environment; (3) from 90 minutes following introduction into the use environment to 180 minutes following introduction into the use environment; and (4) from 300 minutes following introduction into the use environment to 1200 minutes following introduction into the use environment. A composition or method is part of this invention if it meets the dissolution AUC criterion for at least one acceptable time period. In vitro determinations of AUC can be made by plotting drug concentration versus time after dissolving the drug composition in, for example, PBS or MFD solution. Measurement of the AUC in vivo, where the use environment is, for example, the GI tract, is more complicated. This requires sampling the GI fluid as a function of time and thus is less preferred than the in vitro dissolution test or the in vivo relative bioavailability test.

In a preferred embodiment, the composition comprising the mixture provides enhanced relative bioavailability of the drug. In general, compositions or methods that are evaluated using one of the in vitro test methods and found to be a part of the invention will perform well in vivo as well. Bioavailability of drugs in the compositions or methods of the present invention can be tested in vivo in animals, such as mammals and humans using conventional methods for making such a determination. A convenient measure of in vivo bioavailability is the "relative bioavailability," defined as the ratio of the plasma or serum AUC determined from a plot of the plasma or serum drug concentration versus time measured for the composition or method of the present invention to the plasma or serum AUC of a control composition or method that is free of the concentration-enhancing polymer.

A composition of the present invention achieves a relative bioavailability that is at least 1.25. Preferably, the relative bioavailability provided by the composition of the present invention is at least 1.5, more preferably at least 2, and even more preferably at least 3.

Compositions or methods of the invention pass either one or more in vitro dissolution tests or the in vivo relative bioavailability test or both in vitro and in vivo tests.

The concentration of dissolved drug in a dissolution test is typically measured by sampling the test medium and analyzing for the dissolved drug concentration. To avoid relatively large drug particulates which would give an erroneous determination, the test solution is either filtered or centrifuged. "Dissolved drug" is typically taken as that material that either passes a 0.45 μm syringe filter or alternatively the material that remains in the supernatant following centrifugation. Filtration can be conducted using a 13 mm, 0.45 μm polyvinylidine difluoride syringe filter sold by Scientific Resources under the trademark TITAN®. Centrifugation is typically carried out in a polypropylene microcentrifuge tube by centrifuging at about 13,000 G for about 60 seconds. Other similar filtration or centrifugation methods can be employed and useful results obtained. For example, using other types of microfilters may yield values somewhat higher or lower (±10-40%) than that obtained with the filter specified above but will still allow identification of preferred compositions. It will be appreciated by one of ordinary skill that this definition of "dissolved drug" encompasses not only monomeric solvated drug molecules but also a wide range of species such as polymer drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

The Drug

The present invention is useful with any drug capable of being formulated in a solubility-improved form. The term "drug" is conventional, denoting a compound having beneficial prophylactic and/or therapeutic properties when administered to an animal, especially humans. The drug does not need to be sparingly soluble in order to benefit from this invention, although sparingly soluble drugs represent a preferred class for use with the invention. Even a drug that nonetheless exhibits appreciable solubility in the desired environment of use can benefit from the increased solubility/bioavailability made possible by this invention if the addition of the concentration-enhancing polymer can reduce the size of the dose needed for therapeutic efficacy or increase the rate of drug absorption in cases where a rapid onset of the drug's effectiveness is desired.

The present invention finds particular utility when the drug is a "low-solubility drug", meaning that the drug may be either "substantially water-insoluble," which means that the drug has a minimum aqueous solubility at physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL. In general, it may be said that the drug has a dose-to-aqueous solubility ratio greater than 10 mL, and more typically greater than 100 mL, where the drug solubility is the minimum value observed in any physiologically relevant aqueous solution (e.g., those with pH values between 1 and 8) including USP simulated gastric and intestinal buffers.

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, and antiviral agents.

Specific examples of the above and other classes of drugs and therapeutic agents deliverable by the invention are set forth below, by way of example only. Each named drug should be understood to include the neutral form of the drug, pharmaceutically acceptable salts, as well as prodrugs. Specific examples of antihypertensives include prazosin, nifedipine, trimazosin and doxazosin; a specific example of an antianxiety agent is hydroxyzine; a specific example of a blood glucose-lowering agent is glipizide; a specific example of an anti-impotence agent is sildenafil citrate; specific examples of antineoplastics include chlorambucil, lomustine and echinomycin; a specific example of an imidazole-type antineoplastic is tubulazole; specific examples of anti-inflammatory agents include betamethasone, prednisolone, aspirin, flurbiprofen and (+)-N-{4-[3-(4-fluorophenoxy)phenoxy]-2-cyclopenten-1-yl}-N-hydroxyurea; a specific example of a barbiturate is phenobarbital; specific examples of antivirals include acyclovir, nelfinavir, and virazole; specific examples of vitamins/nutritional agents include retinal and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4',6'-trimethylphenoxy)pyridine, pyroxidine, fluoxetine, paroxetine, venlafaxine and sertraline; specific examples of antibiotics include ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, and cinnarizine; specific examples of antipsychotics include ziprasidone, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid and lisinopril; specific examples of tetracycline antibiotics include oxytetracycline and minocycline; specific examples of macrolide antibiotics include erythromycin, azithromycin, clarithromycin, and spiramycin; specific examples of glycogen phosphorylase inhibitors include [R—(R*S*)]-5-chloro-N-(2-hydroxy-3-{methoxymethylamino}-3-oxo-1-(phenyl-methyl)propyl-1H-indole-2-carboxamide and 5-chloro-1H-indole-2-carboxylic acid [(1S)-benzyl-(2R)-hydroxy-3-((3R, 4S)-dihydroxy-pyrrolidin-1-yl-)-3-oxypropyl]amide.

Further examples of drugs deliverable by the invention are the glucose-lowering drug chlorpropamide, the anti-fungal fluconazole, the anti-hypercholesterolemic atorvastatin calcium, the antipsychotic thiothixene hydrochloride, the anxiolytics hydroxyzine hydrochloride and doxepin hydrochloride, the anti-hypertensive amlodipine besylate, the anti-inflammatories piroxicam, valdicoxib, carprofen, and celicoxib, and the antibiotics carbenicillin indanyl sodium, bacampicillin hydrochloride, troleandomycin, and doxycycline hyclate.

The drug is in a solubility-improved form, as defined above in the Summary of the Invention. However, other test media may be used to determine if a drug is in a solubility-improved form, the appropriate medium being different for each drug. Generally speaking, a solubility-improved drug form will provide a maximum concentration in the test medium that is greater than the equilibrium concentration provided by a lower solubility form of the drug in the same test medium. In addition, since the maximum concentration provided by a drug in a test medium is always greater than or equal to the equilibrium concentration provided by the same drug in the same test medium, a drug is considered to be in a solubility-improved form if the maximum concentration provided by the drug in a test media is greater than the maximum concentration provided by a lower-solubility form of the drug.

One must use care when performing an experiment to determine if a drug is in a solubility-improved form, since, as discussed above, the rate at which a solubility-improved drug will convert to its lowest energy state (e.g., the lower solubility form) will vary greatly from drug to drug and from test medium to test medium. As discussed above, the rate at which the solubility-improved form of the drug will convert to its lowest energy form will vary greatly from drug to drug and will be highly dependent on the environment of use under which the drug foam is being evaluated. Therefore, it is desirable to evaluate the solubility improvement of a specific drug form in an in vitro test where the use environment can be carefully controlled. A drug in a solubility-improved form will provide, at least temporarily, a dissolved drug concentration in an in vitro test medium such as distilled water, or PBS or MFD solution at physiologically relevant pH (e.g., from 1 to 8), that is greater than the equilibrium concentration provided by the drug in a lower solubility form. It has been found that distilled water at 37° C. is a convenient use environment for testing the solubility improvement of a drug form to determine whether a drug form is in a solubility-improved form.

In one aspect of the invention, the solubility-improved form of the drug is crystalline and is a highly soluble salt form of the drug. As used herein, "highly soluble salt form" means that the drug is in a salt form that provides in at least one in vitro test medium a maximum concentration of the drug that is greater than the equilibrium concentration provided by the lowest solubility form of the drug. The drug can be any pharmaceutically acceptable salt form of a basic, acidic, or zwitterionic drug that meets this criteria. Examples of salt forms for basic drugs include the hydrochloride, hydrobromide, chloride, bromide, acetate, iodide, mesylate, phosphate, maleate, citrate, sulfate, tartrate, lactate salts and the like. Examples of salt forms for acidic drugs include the sodium, calcium, potassium, zinc, magnesium, lithium, aluminum, meglumine, diethanolamine, benzathine, choline, and procaine salts and the like. These salts can also be used for zwitterionic drugs.

Although essentially any salt form of a specific basic drug may provide a higher drug concentration in a use environment relative to a known lower solubility salt form, it is generally true that the free base or hydrochloride forms of a basic drug have low aqueous solubility relative to other salt forms of the same drug. In addition, in the use environment of the GI tract of a mammal, the free base and hydrochloride forms of a basic drug are commonly the drug forms with which solubilized drug will equilibrate. Thus, where the solubility-improved form of the drug consists only of the basic drug, the solubility-improved form must provide improved drug concentration in a use environment relative to the free base and hydrochloride forms of the drug. Preferred highly soluble salt forms are those salt forms that have aqueous solubility at least 1.25-fold, preferably at least 2-fold, and more preferably at least 5-fold, the aqueous solubility of the more soluble of the crystalline free base and the crystalline hydrochloride salt forms. However, as described below, when the solubility-improved form consists of drug combined with a solubilizer, low-solubility salt foams or even the free base form of the drug may be used.

It should further be noted with reference to low-solubility basic drugs, that they typically have higher solubility in the low pH gastric environment of the stomach relative to the solubility in the intestines or colon that typically have a pH of about 6 to 8. Thus, even though dosing the lowest-solubility known drug form of such a drug to the gastric environment can create a high concentration of dissolved drug, such compositions and methods do not constitute part of this invention.

Preferably, when the solubility-improved form of the drug consists only of a crystalline salt form of a basic drug, the solubility-improved form of the drug provides a drug concentration in gastric fluid or simulated gastric fluid that is greater than the maximum concentration of drug provided by the free base or hydrochloride salt form of the drug in the same fluid. In addition, when the solubility-improved form of the drug consists only of a crystalline basic drug that is solubilized in the presence of gastric fluid (i.e., is more soluble in gastric fluid than in intestinal fluid), a composition comprising the solubility-improved form of the basic drug and a concentration-enhancing polymer preferably provides improved relative bioavailability compared with a control comprising an equivalent amount of the same drug but in a low solubility form (such as the hydrochloride salt form) and an equivalent amount of concentration-enhancing polymer.

An example of a basic drug having a crystalline highly soluble salt form is sertraline. At pH 3, sertraline lactate has a solubility of 256 mg/mL (expressed as the free base) in distilled water, whereas the HCl salt form has a solubility of only 3 mg/mL expressed as the free base. After oral delivery of sertraline lactate to simulated or actual gastric fluid, the drug exchanges the lactate counterion with chloride ions present in gastric fluid and precipitates or crystallizes as the chloride salt and/or free base until an equilibrium concentration is reached. The equilibrium concentration is lower than the maximum concentration provided by sertraline lactate. The drug solubility also decreases as the pH of the surrounding fluid increases due to increased conversion of the drug to the free base form which has a solubility of 0.2 mg/mL at pH 7, which is lower than the solubility of the chloride salt form. Thus, crystalline sertraline lactate is a solubility-improved form relative to the crystalline hydrochloride salt and the crystalline free base form of sertraline.

It should be noted that although distilled water may be used as a test medium for evaluating whether a drug is in a solubility-improved form, it is not generally preferred for use as an in vitro environment of use since its pH and chloride content does not reflect that present in a typical in vivo environment of use. Thus, the solubility-improved form preferably provides an enhanced drug concentration relative to the equilibrium concentration in an in vitro use environment that has a chloride content near that of the anticipated in vivo use environment and a pH between about 6 and 8.

Alternatively, in another separate aspect of the invention, the drug exists in a high-energy crystalline form that has improved solubility relative to a low-energy crystalline form. It is known that some drugs may crystallize into one of several different crystal forms. such crystal forms are often referred to as "polymorphs." As used herein, "a high-energy crystalline form" means that the drug is in a crystal form which provides at least in an in vitro test medium a maximum concentration of the drug that is greater than the equilibrium concentration of the drug provided by another, lower-energy crystalline form.

An example of such a drug is the "A1" form of 5-chloro-1H-indole-2-carboxylic acid [(1S)-benzyl-3-((3R,4S)-dihydroxypyrroldin-1-yl)-(2R)-hydroxy-3-oxpropyl]amide, which has a solubility in PBS of about 480 μg/mL while the "A2" form has a solubility in PBS of only 87 μg/mL.

In yet another separate aspect of the invention, although the drug may be capable of existing in either the amorphous or crystalline form, in the composition it is in the amorphous form. The drug in its amorphous form provides in at least an in vitro test medium a maximum concentration of the drug that is greater than the equilibrium concentration of the drug provided by the drug in crystalline form. An example of such a drug is 5-chloro-1H-indole-2-carboxylic acid [(1S)-benzyl-3-((3R,4S)-dihydroxypyrroldin-1-yl-)-(2R)-hydroxy-3-oxypropyl]amide, the $C_{max}$ of the amorphous form of which is 270 μg/mL, while the $C_{max}$ of its crystalline form is only 160 μg/mL, both as measured in pH 6.5 MFD solution.

In yet another separate aspect of the invention, the solubility-improved form of the drug is a mixture of the drug with a solubilizing agent. The drug/solubilizing agent mixture provides at least temporarily in at least an in vitro test medium a maximum concentration of the drug that is greater than the equilibrium concentration of the drug provided by the drug without the solubilizing agent. An example of such a drug/solubilizing agent mixture is sertraline hydrochloride mixed with citric acid, the equilibrium solubility of which is 28 mg/mL, as compared to 3 mg/mL, for sertraline hydrochloride, both measured at pH 3. Examples of solubilizing agents include surfactants; pH control agents such as buffers, organic acids, organic acid salts, organic and inorganic bases, and organic and inorganic base salts; glycerides; partial glycerides; glyceride derivatives; polyoxyethylene and polyoxypropylene ethers and their copolymers; sorbitan esters; polyoxyethylene sorbitan esters; carbonate salts; alkyl sulfonates; and cyclodextrins. In this aspect, the drug and solubilizing agent are both preferably solid.

There are a variety of factors to consider when choosing an appropriate solubilizing agent for a drug. The solubilizing agent should not interact adversely with the drug. In addition, the solubilizing agent should be highly efficient, requiring minimal amounts to effect the improved solubility. It is also desired that the solubilizing agent have a high solubility in the use environment. For acidic, basic, and zwitterionic drugs, organic acids and organic acid salts, organic and inorganic bases, and organic and inorganic base salts are known to be useful solubilizing agents. It is generally desired that these compounds have a high number of equivalents of acid or base per gram. In addition, it is generally desirable that the acid or base solubilizing agent be chosen such that the salt formed by the ionic form of the drug and the corresponding conjugate acid or base of the solubilizing agent have a high solubility. The selection of solubilizing agent will therefore be highly dependent on the properties of the drug.

In yet another separate aspect of the invention, the solubility-improved form of the drug is a solution or suspension of a drug substantially dissolved or suspended in a liquid to a concentration that is at least 10-fold an equilibrium concentration of the drug in the use environment. Examples of liquids suitable for this solubility-improved form of drug include water-immiscible triglyceride vegetable oils such as safflower oil, sesame oil, corn oil, castor oil, coconut oil, cottonseed oil, soybean oil, olive oil and the like; water-immiscible refined and synthetic and semisynthetic oils such as mineral oil, the triglycerides known as MIGLYOLs®, including triglycerides of caprylic/capric acids and triglycerides of caprylic/capric/linoleic acids, long-chain triglyceride oils such as triolein, other mixed-chain triglycerides which are liquid at room temperature, monoglycerides, diglycerides, and mixtures of mono-, di-, and triglycerides; fatty acids and esters; water-miscible alcohols, glycerin and propyleneglycol; and water-miscible polyethyleneglycols (PEGS) which are liquid at the temperature of the use environment (which is typically about 35 to 40° C.), such as PEG-400. Examples of such materials that are commercially available include corn oil, propylene glycol, CREMOPHOR RH-40 (polyoxy)-40 hydrogenated castor oil), LABRAFIL M 2125 (linoleoyl polyoxyl-6 glycerides), and 1944 (oleoyl polyoxyl-6 glycerides), ethanol, PEG 400, Polysorbate 80, glycerin, peppermint oil, soybean oil (long chain triglyceride), sesame oil (long chain triglyceride), propylene carbonate, and tocopheryl TPGS. Other key commercial materials include MIGLYOL 812 (caprylic/capric triglycerides), oleic acid, olive oil (long chain triglyceride), CAPMUL MCM (medium chain monoglyceride), CAPMUL PG-8 (propylene glycol capyrlyl mono and diglycerides), CREMOPHOR EL (polyoxyl 35 castor oil), LABRASOL (caprylocaproyl polyoxyl-8 glycerides), triacetin (acetyl triglyceride), MAISINE 35-1 (glyceryl monolinoleate), OLICINE (glyceryl mono oleate/linoleate), PECEOL (glyceryl monooleate), TRANSCUTOL P (diethylene glycol monoethylether), PLUROL Oleique CC (polyglyceryl-6 dioleate), LAUROGLYCOL 90 (propylene glycol monolaureate), CAPRYOL 90 (propylene glycol monocaprylate), MYVACETS (acetylated monoglycerides), ARLACELS (sorbitan fatty acid ester), PLURONICS (copolymers of propylene and ethylene oxide), BRIJ 30 (polyoxylethylene 4 lauryl ether), GELUCIRE 44/14 (lauroyl polyoxyl-32 glycerides), and GELUCIRE 33/01 (glycerol esters of fatty acids). Mixtures of these and other related materials are acceptable as long as they are liquid at the temperature of the use environment which is typically about 35 to 40° C.

Concentration-Enhancing Polymers

Concentration-enhancing polymers suitable for use in the various aspects of the present invention should be inert, in the sense that they do not chemically react with the drug in an adverse manner, and should have at least some solubility in aqueous solution at physiologically relevant pHs (e.g. 1-8). Almost any neutral or ionizable polymer that has an aqueoussolublitity of at least 0.1 mg/mL over at least a portion of the pH range of 1-8 may be suitable.

A preferred class of concentration-enhancing polymers comprises ionizable and nonionizable cellulosic polymers (including those with ether or ester or a mixture of ester and ether substituents and copolymers thereof, including both so-called "enteric" and "non-enteric" polymers); and vinyl polymers and copolymers having substituents of hydroxyl, alkylacyloxy, and cyclicamido. It is also preferred that the concentration-enhancing polymers be "amphiphilic" in nature, meaning that the polymer has hydrophobic and hydrophilic portions.

Amphiphilic and/or ionizable polymers are preferred because it is believed that such polymers tend to have relatively strong interactions with the drug and may promote the formation of the various types of polymer/drug assemblies described previously. In addition, the repulsion of the like charges of the ionized groups of such polymers may serve to limit the size of the polymer/drug assemblies to the nanometer or submicron scale. For example, while not wishing to be bound by a particular theory, such polymer/drug assemblies may comprise hydrophobic drug clusters surrounded by the concentration-enhancing polymer with the polymer's hydrophobic regions turned inward towards the drug and the hydrophilic regions of the polymer turned outward toward the aqueous environment. Alternatively, depending on the specific chemical nature of the drug, the ionized functional groups of the polymer may associate, for example, via ion pairing or hydrogen bonds, with ionic or polar groups of the drug. In the case of ionizable polymers, the hydrophilic regions of the polymer would include the ionized functional groups. Such drug/concentration-enhancing polymer assemblies in solution may well resemble charged polymeric micellar-like structures. In any case, regardless of the mechanism of action, the inventors have observed that such amphiphilic polymers, particularly ionizable cellulosic polymers such as those listed below, have been shown to interact with drug so as to inhibit its crystallization.

Amphiphilic cellulosics may be prepared by substituting the cellulosic at any or all of the 3 hydroxyl substituents present on each saccharide repeat unit with at least one relatively hydrophobic substituent. Hydrophobic substituents may be essentially any substituent that, if substituted to a high enough level or degree of substitution, can render the cellulosic polymer essentially aqueous insoluble. Hydrophilic regions of the polymer can be either those portions that are relatively unsubstituted, since the unsubstituted hydroxyls are themselves relatively hydrophilic, or those regions that are substituted with hydrophilic substituents. Examples of hydrophobic substitutents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic groups include ether- or ester-linked nonionizable groups such as the hydroxy alkyl substituents hydroxy ethyl, hydroxy propyl, and the alkyl ether groups such as ethoxyethoxy or methoxyethoxy. Particularly preferred hydrophilic substituents are those that are ether- or ester-linked to the cellulose and, following substitution have ionizable groups such as carboxylic acids, thiocarboxylic acids, substituted phenoxy groups, amines, phosphates or sulfonates. Specific substituents include, succinate, citrate, phthalate, trimellitate, hydroxyphenoxy, aminoethoxy, thiosuccinate, diethylaminoethoxy, trimethylamino ethoxy, sulphonate ethoxy, and phosphate ethoxy.

It should be noted that a polymer name such as "cellulose acetate phthalate" (CAP) refers to any of the family of cellulosic polymers that have acetate and phthalate groups attached via ester linkages to a significant fraction of the cellulosic polymer's hydroxyl groups. Generally, the degree of substitution of each substituent group can range from 0.1 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate substituted, the phthalate degree of substitution is 3. Also included within each polymer family type are cellulosic polymers that have additional substituents added in relatively small amounts that do not substantially alter the performance of the polymer.

It should also be noted that in the polymer nomenclature herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

Specific examples of cellulosic polymers that meet the definition of amphiphilic, having hydrophilic and hydrophobic regions include polymers such as CAP and cellulose acetate trimellitate (CAT) where the cellulosic repeat units that have one or more acetate substituents are hydrophobic relative to those that have no acetate substituents or have one or more ionized phthalate or trimellitate substituents; and polymers such as hydroxypropyl methyl cellulose (HPMC) or hydroxypropyl cellulose acetate (HPCA) where cellulosic repeat units that have relatively high numbers of methoxy or acetate substituents relative to the unsubstituted hydroxyl or hydroxypropyl substituents constitute hydrophobic regions relative to other repeat units on the polymer.

Non-cellulosic polymers that meet this definition of amphiphilicity are copolymers of a relatively hydrophilic and a relatively hydrophobic monomer. Examples include acrylate and methacrylate copolymers. Exemplary commercial grades of such copolymers include the EUDRAGITS, which are copolymers of methacrylates and acrylates manufactured by Rohm Tech Inc., of Malden, Mass.

Exemplary ionizable polymers that are at least partially ionized at physiologically relevant pHs that may be used as the concentration-enhancing polymer include: hydroxypropyl methyl cellulose acetate succinate, hydroxypropyl methyl cellulose succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, carboxymethyl ethyl cellulose and carboxylic acid-functionalized polymethacrylates.

Exemplary non-ionizable polymers that may be used as the concentration-enhancing polymers include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, hydroxyethyl ethyl cellulose, polyvinyl alcohols that have at least a portion of their repeat units in the unhydrolyzed (vinyl acetate) form, polyvinyl alcohol polyvinyl acetate copolymers, polyethylene glycol, polyethylene glycol polypropylene glycol copolymers, polyvinyl pyrrolidone, and polyethylene polyvinyl alcohol copolymers and chitan.

One class of polymers which meets the requirements of the present invention includes cellulosic polymers with an ester- or ether-linked aromatic substituent in which the polymer has a degree of substitution of at least 0.1. Exemplary aromatic substituents include benzoate, phenoxy and ethoxy phenyl. For such aromatic-substituted polymers to also have the requisite aqueous solubility, it is also desirable that sufficient hydrophilic groups such as hydroxypropyl or carboxylic acid functional groups be attached to the polymer. Such carboxylic acid groups can be ether-linked to the polymer as is the case for carboxy ethyl groups, or they may be attached via ester linkages such as for succinate groups. The carboxylic acid and aromatic group can be combined in a single substituent as is the case, for example for carboxylic acid-substituted aromatic groups that may be attached via ester linkages which include phthalate, trimellitate, the various isomers of pyridinedicarboxylic acid, terephthalate, isophthalate and alkyl-substituted derivatives of these groups. Exemplary carboxylic acid-substituted aromatic groups that may be attached via ether linkages include salicylic acid, alkoxybenzoic acids such as ethoxy benzoic acid or propoxybenzoic acid, the various isomers of alkoxyphthalic acid such as ethoxyphthalic acid and ethoxyisophthalic acid, and the various isomers of alkoxynicotinic acid such as ethoxynicotinic acid, and ethoxypicolinic acid.

A particularly desirable subset of cellulosic ionizable polymers are those that possess both a carboxylic acid functional aromatic substituent and an alkylate substituent. Exemplary polymers include cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another particularly desirable subset of cellulosic ionizable polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, and hydroxyethyl cellulose acetate succinate.

Even more preferred polymers are hydroxypropyl methyl cellulose acetate succinate, cellulose acetate phthalate, hydroxy propyl methyl cellulose phthalate, methyl cellulose acetate phthalate, hydroxypropyl cellulose acetate phthalate, cellulose acetate trimellitate, cellulose acetate terephthalate and cellulose acetate isophthalate. The most preferred polymers are hydroxypropyl methyl cellulose acetate succinate, hydroxypropyl methyl cellulose phthalate, cellulose acetate phthalate, and cellulose acetate trimellitate.

While specific polymers have been discussed as being suitable for use in the mixtures of the present invention, blends of such polymers may also be suitable. Thus the term "concentration-enhancing polymer" is intended to include blends of polymers in addition to a single species of polymer.

Preparation of Compositions

The compositions of the present invention may be prepared by dry- or wet-mixing the drug or drug mixture with the concentration-enhancing polymer to form the composition. Mixing processes include physical processing as well as wet-granulation and coating processes. Any conventional mixing method that does not substantially convert the drug and polymer to a molecular dispersion may be used.

For example, mixing methods include convective mixing, shear mixing, or diffusive mixing. Convective mixing involves moving a relatively large mass of material from one part of a powder bed to another, by means of blades or paddles, revolving screw, or an inversion of the powder bed. Shear mixing occurs when slip planes are formed in the material to be mixed. Diffusive mixing involves an exchange of position by single particles. These mixing processes can be performed using equipment in batch or continuous mode. Tumbling mixers (e.g., twin-shell) are commonly used equipment for batch processing. Continuous mixing can be used to improve composition uniformity.

Milling may also be employed to prepare the compositions of the present invention. Milling is the mechanical process of reducing the particle size of solids (comminution). Because in some cases milling may alter crystalline structure and cause chemical changes for some materials, milling conditions are generally chosen which do not alter the physical form of the drug in the sense that the drug and polymer are not mixed at the molecular level to form a dispersion of polymer and drug. The most common types of milling equipment are the rotary cutter, the hammer, the roller and fluid energy mills. Equipment choice depends on the characteristics of the ingredients in the drug form (e.g., soft, abrasive, or friable). Wet- or dry-milling techniques can be chosen for several of these processes, also depending on the characteristics of the ingredients (e.g. drug stability in solvent). The milling process may serve simultaneously as a mixing process if the feed materials are heterogeneous. Conventional mixing and milling processes suitable for use in the present invention are discussed more fully in Lachman, et al., *The Theory and Practice of Industrial Pharmacy* (3d Ed. 1986). The components of the compositions of this invention may also be combined by dry- or wet-granulating processes as long as granulating conditions are chosen that do not transform a substantial portion of the drug into a molecular dispersion of polymer and drug.

In addition to the physical mixtures described above, the compositions of the present invention may constitute any device or collection of devices that accomplishes the objective of delivering to the use environment both the drug in a solubility-improved form and the concentration-enhancing polymer. Thus, in the case of oral administration to a mammal, the dosage foam may constitute a layered tablet wherein one or more layers comprise the solubility-improved form of the drug and one or more other layers comprise the concentration-enhancing polymer. Alternatively, the dosage form may be a coated tablet wherein the tablet core comprises the solubility-improved drug form and the coating comprises the concentration-enhancing polymer. In addition, the solubility-improved drug form and the concentration-enhancing polymer may even be present in different dosage forms such as tablets or beads and may be administered simultaneously or separately as long as both the solubility-improved drug form and concentration-enhancing polymer are administered in such a way that the drug and polymer can come into contact in the use environment. When the solubility-improved drug form and the concentration-enhancing polymer are administered separately it is generally preferable to deliver the polymer prior to the drug.

The amount of concentration-enhancing polymer relative to the amount of drug present in the mixtures of the present invention depends on the drug and concentration-enhancing polymer and may vary widely from a drug-to-polymer weight ratio of 0.01 to 5. However, in most cases it is preferred that the drug-to-polymer ratio is greater than 0.05 and less than 2.5 and often the enhancement in drug concentration or relative bioavailability is observed at drug-to-polymer ratios of 1 or less or for some drugs even 0.2 or less. The minimum drug:polymer ratio that yields satisfactory results varies from drug to drug and is best determined in the in vitro and/or in vivo dissolution tests.

In general, to maximize the drug concentration or relative bioavailability of the drug, lower drug-to-polymer ratios are preferred. At low drug-to-polymer ratios, there is sufficient concentration-enhancing polymer available in solution to ensure the inhibition of the precipitation or crystallization of drug from solution and, thus, the average concentration of drug is much higher. For high drug/polymer ratios, not enough concentration-enhancing polymer may be present in solution and drug precipitation or crystallization may occur more readily. However, the amount of concentration-enhancing polymer that can be used in a dosage form is often limited by the total mass requirements of the dosage form. For example, when oral dosing to a human is desired, at low drug/polymer ratios the total mass of drug and polymer may be unacceptably large for delivery of the desired dose in a single tablet or capsule. Thus, it is often necessary to use drug/polymer ratios that are less than optimum in specific dosage forms to provide a sufficient drug dose in a dosage from that is small enough to be easily delivered to a use environment.

Excipients and Dosage Forms

Although the key ingredients present in the compositions of the present invention are simply the drug to be delivered in its solubility-improved form and the concentration-enhancing polymer(s), the inclusion of other excipients in the composition may be useful. These excipients may be utilized with the drug/polymer mixture in order to formulate the mixture into tablets, capsules, suspensions, powders for suspension, creams, transdermal patches, depots, and the like. Drug and concentration-enhancing polymer can be added to other dosage form ingredients in essentially any manner that does not substantially alter the drug. In addition, as described above, the drug in its solubility-improved form and the concentration-enhancing polymer may be mixed with excipients separately to form different beads, or layers, or coatings, or cores or even separate dosage forms.

One very useful class of excipients is surfactants. Suitable surfactants include fatty acid and alkyl sulfonates; commercial surfactants such as benzethanium chloride (HYAMINE® 1622, available from Lonza, Inc., Fairlawn, N.J.); DOCUSATE SODIUM (available from Mallinckrodt Spec. Chem., St. Louis, Mo.); polyoxyethylene sorbitan fatty acid esters (TWEEN®, available from ICI Americas Inc., Wilmington, Del.); LIPOSORB® P-20 (available from Lipochem Inc., Patterson N.J.); CAPMUL® POE-0 (available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, formation of micelles or adsorbing to the surface of solid drug, crystalline or amorphous. These surfactants may comprise up to 5 wt % of the composition.

The addition of pH modifiers such as acids, bases, or buffers may also be beneficial, retarding the dissolution of the composition (e.g., acids such as citric acid or succinic acid when the polymer is anionic) or, alternatively, enhancing the rate of dissolution of the composition (e.g., bases such as sodium acetate or amines when the polymer is anionic).

Conventional matrix materials, complexing agents, solubilizers, fillers, disintegrating agents (disintegrants), or binders may also be added as part of the composition itself or added by granulation via wet or mechanical or other means. These materials may comprise up to 90 wt % of the composition.

Examples of matrix materials, fillers, or diluents include lactose, mannitol, xylitol, microcrystalline cellulose, dibasic calcium diphosphate, and starch.

Examples of disintegrants include sodium starch glycolate, sodium alginate, carboxy methyl cellulose sodium, methyl cellulose, and croscarmellose sodium.

Examples of binders include methyl cellulose, microcrystalline cellulose, starch, and gums such as guar gum, and tragacanth.

Examples of lubricants include magnesium stearate and calcium stearate.

Other conventional form excipients may be employed in the compositions of this invention, including those excipients well-known in the art. Generally, excipients such as pigments, lubricants, flavorants, and so forth may be used for customary purposes and in typical amounts without adversely affecting the properties of the compositions. These excipients may be utilized in order to formulate the composition into tablets, capsules, suspensions, powders for suspension, creams, transdermal patches, and the like.

Compositions of this invention may be used in a wide variety of dosage forms for administration of drugs. Exemplary dosage forms are powders or granules that may be taken orally either dry or reconstituted by addition of water to form a paste, slurry, suspension or solution; tablets; capsules; multiparticulates; and pills. Various additives may be mixed, ground, or granulated with the compositions of this invention to form a material suitable for the above dosage forms.

In some cases, the overall dosage form or particles, granules or beads that make up the dosage form may have superior performance if coated with an enteric polymer to prevent or retard dissolution until the dosage form leaves the stomach. Exemplary enteric coating materials include HPMCAS, HPMCP, CAP, CAT, carboxylic acid-functionalized polymethacrylates, and carboxylic acid-functionalized polyacrylate.

Compositions of this invention may be administered in a controlled release dosage form. In one such dosage form, the composition of the drug in the solubility-improved form and concentration-enhancing polymer is incorporated into an erodible polymeric matrix device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or "matrix" that entraps the mixture of solubility-improved drug and concentration-enhancing polymer. The aqueous-swollen matrix gradually erodes, swells, disintegrates or dissolves in the environment of use, thereby controlling the release of the drug mixture to the environment of use.

Alternatively, the compositions of the present invention may be administered by or incorporated into a non-erodible matrix device.

Alternatively, the drug mixture of the invention may be delivered using a coated osmotic controlled release dosage form. This dosage form has two components: (a) the core which contains an osmotic agent and the drug in a solubility-improved form and the concentration-enhancing polymer either mixed or in separate regions of the core; and (b) a non-dissolving and non-eroding coating surrounding the core, the coating controlling the influx of water to the core from an aqueous environment of use so as to cause drug release by extrusion of some or all of the core to the environment of use. The osmotic agent contained in the core of this device may be an aqueous-swellable hydrophilic polymer, osmogen, or osmagent. The coating is preferably polymeric, aqueous-permeable, and has at least one delivery port.

Alternatively, the drug mixture of the invention may be delivered via a coated hydrogel controlled release dosage form having three components: (a) a composition containing the drug in the solubility-improved form, (b) a water-swellable composition wherein the water-swellable composition is in a separate region within a core formed by the drug-containing composition and the water-swellable composition, and (c) a coating around the core that is water-permeable, water-insoluble, and has a least one delivery port therethrough. In use, the core imbibes water through the coating, swelling the water-swellable composition and increasing the pressure within the core, and fluidizing the drug-containing composition. Because the coating remains intact, the drug-containing composition is extruded out of the delivery port into an environment of use. The concentration-enhancing polymer may be delivered in a separate dosage form, may be included in the drug-containing composition or may constitute all or part of a coating applied to the dosage form.

When the solubility-improved drug form is a solution or suspension of the drug in an aqueous or organic liquid the composition can be delivered via soft gelatin or hard gelatin capsules, which are known and well understood in the art. These dosage forms comprise a water-soluble soft or hard gelatin exterior shell that encapsulates a vehicle in which a drug has been dissolved and/or suspended. Examples of vehicles used for this purpose are discussed above. Here, the concentration-enhancing polymer can be dissolved or suspended in the aqueous or organic liquid. Alternatively, the soft or hard gelatin exterior shell can be coated with or made from the concentration-enhancing polymer.

Alternatively, the compositions of the present invention may be co-administered, meaning that the drug in its solubility-improved form can be administered separately from, but within the same general time frame as, the concentration-enhancing polymer. Thus, a drug in a solubility-improved form can, for example, be administered in its own dosage form which is taken at approximately the same time as the concentration-enhancing polymer which is in a separate dosage form. If administered separately, it is generally preferred to administer both the drug in its solubility-improved form and the concentration-enhancing polymer within 60 minutes of each other, so that the two are present together in the environment of use. When not administered simultaneously, the concentration-enhancing polymer is preferably administered prior to the solubility-improved form of the drug.

In addition to the above additives or excipients, use of any conventional materials and procedures for preparation of suitable dosage forms using the compositions of this invention known by those skilled in the art are potentially useful.

Other features and embodiments of the invention will become apparent from the following examples which are given for illustration of the invention rather than for limiting its intended scope.

EXAMPLES 1-3

These examples demonstrate a composition comprising a mixture of an amorphous drug and concentration-enhancing polymer, as well as an in vitro dissolution test known as the "microcentrifuge" method. This method was used to test the dissolution of mixtures of the MF grade of hydroxypropyl methyl cellulose acetate succinate (HPMCAS-MF, containing 23.4% methoxyl, 7.2% hydroxypropoxy, 9.4% acetyl, 11.0% succinoyl, average molecular weight of 10,000 to 20,000, manufactured by Shin Etsu) and amorphous 5-chloro-1H-indole-2-carboxylic acid [(1S)-benzyl-3-((3R, 4S)-dihydroxypyrroldin-1-yl-)-(2R)-hydroxy-3-oxypropyl] amide (a glycogen phosphorylase inhibitor) (Drug 1). The maximum concentration of Drug 1, $C_{max}$, for the amorphous form in pH 6.5 MFD solution is 270 µg/mL, while the $C_{max}$ of the crystalline form is only 160 µg/mL.

Amorphous drug (here the solubility-improved form) was prepared by adding 10 g of Drug 1 to 118 g of acetone and 6.2 g of water. Solvent was rapidly removed from this solution by spray-drying. During spray-drying, the drug solution was placed in a pressure vessel that delivered the drug solution at a controlled rate to a commercial spray dryer (Mobile Minor Hi-Tec for Non-Aqueous Feed Spray Dryer, manufactured by Niro A/S, Soburg, Denmark). The Niro spray dryer consists of a two-fluid nozzle atomizer that fits into the top of a drying chamber. Nitrogen atomizing gas was delivered to the nozzle at 2.7 bar and the drug solution was delivered at a flow rate of 197 g/min. Drying gas (nitrogen heated to 197° C.) was delivered to the drying chamber through an inlet duct that surrounds the two-fluid nozzle. The spray-dried material exited the chamber with the drying gas through transport ducts and passed into a cyclone. At the top of the cyclone, an exhaust vent allowed the nitrogen and evaporated solvent to escape. The spray-dried material was collected in a canister. The material was a dry, white, substantially amorphous powder. The yield of amorphous drug was 43%.

In a 37° C. temperature-controlled box, 3.6 mg of amorphous Drug 1 was accurately weighed into eight empty microcentrifuge tubes (polypropylene, Sorenson Bioscience, Inc.). The theoretical maximum supersaturated concentration of compound in solution was 2000 µg/mL (3.6 mg drug [1000 µg/1 mg]/1.8 mL=2000 µg/mL). (The theoretical maximum supersaturated concentration which is abbreviated as theoretical $C_{max}$ represents the concentration if all of the compound was dissolved.) Tests were performed in duplicate.

Control 1 consisted only of amorphous Drug 1 in Tubes 1 and 2. For Example 1, 1.2 mg of HPMCAS-MF was added to Tubes 3 and 4. For Example 2, 3.6 mg of HPMCAS-MF was added to Tubes 5 and 6. For Example 3, 10.8 mg of HPMCAS-MF was added to Tubes 7 and 8. These four groups of samples represented a Control 1 of amorphous Drug 1 and compositions 1, 2 and 3 having drug:polymer ratios of 3:1, 1:1, and 1:3, respectively.

At time equal to 0, 1.8 mL of a 37° C. PBS solution (8.2 mM NaCl, 1.1 mM $Na_2HPO_4$, 4.7 mM $KH_2PO_4$, pH 6.5, 290 mOsm/kg) was added to each tube. The centrifuge tubes were closed and a timer was started. The tubes were then mixed continuously at the highest speed of a Fisher Vortex Genie 2 mixer for 60 seconds. The tubes were then transferred to a centrifuge (Marathon, Model Micro A), and then centrifuged at 13,000 G for 60 seconds. At 4 minutes, a 50-μL sample was removed from the solids-free supernatant in the centrifuge tubes via pipette. Solids in the centrifuge tube were resuspended by mixing the sample continuously on the vortex mixer for 30 seconds. The centrifuge tube was returned to the centrifuge and allowed to stand undisturbed until the next sample was taken. Each sample was centrifuged, sampled, and resuspended as described above. Each sample was diluted by adding 50 AL of supernatant to 250 AL of methanol, and the concentration of the compound was determined by high-performance liquid chromatography (HPLC) (Hewlett Packard 1100, Zorbax SB C18 column, 35% acetonitrile (ACN)/65% $H_2O$, absorbance measured at 297 nm with a diode array spectrophotometer).

Samples were taken after 4, 10, 20, 40, 90, 180, and 1200 minutes as described above, analyzed, and compound concentrations were calculated. The data are summarized in Table 1.1. Each of Examples 1-3 sustained the concentration of drug in solution above the equilibrium concentration provided by Control 1 for greater than 20 hours (1200 minutes).

TABLE 1.1

| | [Drug 1] (μg/mL) | | | |
|---|---|---|---|---|
| Time (mins) | Control 1 (Drug Alone) | 1 (3:1) Drug 1:HPMCAS-MF | 2 (1:1) Drug 1:HPMCAS-MF | 3 (1:3) Drug 1:HPMCAS-MF |
| 4 | 574 | 714 | 754 | 998 |
| 10 | 507 | 736 | 739 | 1032 |
| 20 | 286 | 695 | 835 | 1064 |
| 40 | 217 | 690 | 845 | 1132 |
| 90 | 187 | 728 | 897 | 1184 |
| 180 | 208 | 683 | 917 | 1301 |
| 1200 | 203 | 440 | 626 | 1377 |

The maximum concentration of drug reached ($C_{max}$), the dissolution area under a curve plotting the concentration of Drug 1 versus time from 0 to 90 minutes ($AUC_{90}$), and the concentration after 20 hours, or 1200 minutes, ($C_{1200}$) were calculated and are reported in Table 1.2, together with the theoretical $C_{max}$. The theoretical $C_{max}$ is the drug concentration that would be obtained if all of Drug 1 was dissolved. That is, the total mass of active drug dosed to the test solution in μg divided by the total volume of the test solution in mL. As is apparent, the $C_{max}$ for Examples 1, 2 and 3 was 1.28-fold, 1.6-fold and 2.4-fold that of amorphous drug alone (Control 1), while the $AUC_{90}$ for Examples 1, 2 and 3 was 2.7-, 3.0-, and 4.2-fold that of the amorphous drug alone (Control 1).

TABLE 1.2

| Example | $C_{max}$ (μg/mL) | $AUC_{90}$ (min*μg/mL) | $C_{1200}$ (μg/mL) | Theoretical $C_{max}$ (μg/mL) |
|---|---|---|---|---|
| Control 1 (Drug 1 only) | 574 | 23,500 | 203 | 2000 |
| 1 (3:1 Drug 1 HPMCAS-MF) | 736 | 62,200 | 440 | 2000 |
| 2 (1:1 Drug 1 HPMCAS-MF) | 917 | 74,200 | 626 | 2000 |
| 3 (1:3 Drug 1 HPMCAS-MF) | 1377 | 98,400 | 1377 | 2000 |

EXAMPLE 4

This example demonstrates another composition of amorphous Drug 1 and a concentration-enhancing polymer. Amorphous Drug 1 was prepared as described in Example 1, and dissolution was measured for an oral powder for constitution (OPC) suspension in an in vitro test known as the "gastric buffer to PBS transfer test." The test mimics oral administration of an OPC dosage form by exposure to a small volume of acidic fluid (gastric buffer) for 30 minutes followed by exposure to PBS solution (intestinal buffer).

For these tests, 40 mL of gastric buffer (0.084 M HCl, 0.058 M NaCl, 7.0 atm, pH 1.2) was added to a 500-mL dissoette flask at 37° C. Control 2 consisted of 0.6 g of amorphous Drug 1. Example 4 consisted of 0.6 g of amorphous Drug 1 and 1.8 g of HPMCAS-MF. The constituents of Control 2 and Example 4 were weighed into OPC bottles, respectively, and 15 mL of 2 wt % Tween 80 was added to each bottle. Each solution was mixed for 2 minutes. Deionized water (105 mL) was added to each OPC bottle, each bottle was inverted twice, and the contents were added to respective dissoette flasks. Each OPC bottle was rinsed into the respective dissoette flask twice, each time using 60 mL of deionized water. Each dissoette flask was stirred at 100 rpm for 30 minutes; a sample was taken from each after 25 minutes. After 30 minutes of stirring, 0.55 mL of 10% NaOH and 200 mL of 2.5×PBS (PBS solution with 2.5 times the standard buffer salt concentration) were added to each dissoette flask. The pH of the solution within each flask was adjusted to 6.5 with 10% NaOH.

Samples were taken at 4, 10, 20, 40, 90, 180, and 1200 minutes following adjustment of the pH to 6.5. This was done by removing four drops from each dissoette flask and placing the drops in a respective microcentrifuge tube. Samples were centrifuged for 1 minute at 13,000 G. Supernatant (50 μL) was removed and added to 250 μL of Methanol in an HPLC vial. Drug concentrations were measured using HPLC. The results are shown in Table 2.1.

TABLE 2.1

| | [Drug 1] (μg/mL) | |
|---|---|---|
| Time (mins) | Control 2: (Drug 1 only) | Example 4 (1:2 Drug 1:HPMCAS-MF) |
| 0 | 720 | 427 |
| 4 | 359 | 857 |
| 10 | 357 | 880 |
| 20 | 325 | 893 |
| 40 | 291 | 886 |
| 90 | 263 | 923 |

TABLE 2.1-continued

| Time (mins) | Control 2: (Drug 1 only) | Example 4 (1:2 Drug 1:HPMCAS-MF) |
|---|---|---|
| 180 | 251 | 765 |
| 1200 | 237 | 528 |

The $C_{max}$ the $AUC_{180}$ (AUC calculated from 0 to 180 minutes), the $C_{1200}$ and the theoretical $C_{max}$ are shown in Table 2.2.

TABLE 2.2

| Example | $C_{max}$ (µg/mL) | $AUC_{180}$ (min*µg/mL) | $C_{1200}$ (µg/mL) | Theoretical (µg/mL) |
|---|---|---|---|---|
| Control 2 (Drug 1 only) | 720 | 50,800 | 237 | 1250 |
| Example 4 (1:2 Drug 1:HPMCAS-MF) | 923 | 155,600 | 528 | 1250 |

As the data show, $C_{max}$ for Example 4 consisting of the amorphous drug with HPMCAS-MF polymer was 1.28-fold that of Control 2, consisting of the amorphous drug alone, while the $AUC_{180}$ for Example 4 was 3-fold the $AUC_{180}$ for the Control 2.

EXAMPLES 5-9

These examples demonstrate compositions of amorphous Drug 1 mixed with varying ratios of a concentration-enhancing polymer. Amorphous Drug 1 (15 mg) was added to microcentrifuge tubes containing 1.5 mL of PBS solution and varying concentrations of HPMCAS-MF. Dissolution performance was measured at 37° C. using the microcentrifuge method described in Example 1. Drug concentration was measured at 1.5 hours and at 20 hours for each polymer concentration. The results are shown in Table 3.

TABLE 3

| Example | Drug 1:HPMCAS-MF Ratio (w:w) | [Drug] 1.5 hr. (µg/mL) | [Drug] 20 hr (µg/mL) |
|---|---|---|---|
| Control 3 | No HPMCAS-MF | 224 | 196 |
| 5 | 20:1 | 447 | 289 |
| 6 | 10:1 | 487 | 293 |
| 7 | 5:1 | 4928 | 1550 |
| 8 | 1:1 | 7453 | 5431 |
| 9 | 1:2 | 8099 | 7451 |

The data in Table 3 show that even at low polymer concentrations, some concentration-enhancement was observed. However, the effect increased with decreasing drug:polymer weight ratio. This shows that to maximize the concentration enhancement, a sufficient amount of polymer must be present in the composition.

EXAMPLES 10-11

These examples demonstrate compositions of a drug in a highly soluble salt form (the solubility-improved form) and a concentration-enhancing polymer. As discussed in the section describing solubility-improved drugs, sertraline lactate (Drug 2) is a soluble salt form of the anti-depressant drug sertraline. The solubility of sertraline lactate is 256 mg/mL (calculated using the molecular weight of the free base which is 306 g/mol), while the solubility of the hydrochloride salt is only 3 mg/mL (calculated using the molecular weight of the free base), both measured at pH 3.

For these tests, 1.8 mg sertraline lactate was added to 0.9 mL HPLC water in each of six microcentrifuge tubes. For Control 4, 0.9 mL 2×PBS (PBS solution with 2 times the standard buffer salt concentration), adjusted to pH 8.0, was added to Tubes 1 and 2. For Example 10, 0.9 mL 2×PBS (pH 8.0) containing 3.6 mg of HPMCAS-MF was added to Tubes 3 and 4. For Example 11, 0.9 mL 2×PBS (pH 8.0) containing 3.6 mg of CAT was added to Tubes 5 and 6. Control 4 did not contain concentration-enhancing polymer.

Dissolution performance was measured at 37° C. using the microcentrifuge method described in Example 1. Samples were taken after 4, 10, 20, 40, 90, and 180 minutes as described in Example 1. Samples were diluted in 35% $H_2O$/65% ACN (vol./vol.), and analyzed by HPLC. The mobile phase was 35 vol. % 0.025 M triethylamine with 0.05M acetic acid in HPLC water in ACN. The analytical column used was a Phenomenex ODS 20, and the drug concentration was determined using diode array detection at 230 nm. Results of the microcentrifuge test are shown in Table 4.1.

TABLE 4.1

| | [Drug 2] (µg/mL) | | |
|---|---|---|---|
| Time (mins) | Control 4 (Drug 2 only) | Example 10 (1:2 Drug 2:HPMCAS-MF) | Example 11 (1:2 Drug 2:CAT) |
| 4 | 101 | 617 | 456 |
| 10 | 89 | 550 | 376 |
| 20 | 72 | 459 | 321 |
| 40 | 67 | 413 | 286 |
| 90 | 63 | 373 | 283 |
| 180 | 60 | 341 | 245 |

These data show that for the compositions containing a concentration-enhancing polymer the maximum concentration of Drug 2 was 4.5-fold to 6.1-fold that of Control 4.

TABLE 4.2

| Example | $C_{max}$ (µg/mL) | $AUC_{180}$ (min*µg/mL) | Theoretical $C_{max}$ (µg/mL) |
|---|---|---|---|
| Control 4 (Drug 2 only) | 101 | 11,700 | 1000 |
| 10 (1:2 Drug 2:HPMCAS-MF) | 617 | 70,300 | 1000 |
| 11 (1:1 Drug 2:CAT) | 456 | 50,900 | 1000 |

Table 4.2 shows the $AUC_{180}$ for the composition containing HPMCAS-MF was 6.0-fold that of the Control 4, and the $AUC_{180}$ for the composition containing CAT was 4.4-fold that of Control 4.

EXAMPLES 12-14

These examples demonstrate a composition comprising a drug in a highly soluble salt form (here the solubility-improved form) and a concentration-enhancing polymer. Ziprasidone mesylate (Drug 3) is the soluble salt form of the antipsychotic drug ziprasidone. For these tests, 0.5 mg drug was added to each of 8 microcentrifuge tubes. For Control 5, no concentration-enhancing polymer was added to Tubes 1 and 2. For Example 12, 1.0 mg of CAT was added to Tubes 3 and 4. For Example 13, 1.0 mg of CAP (NF grade from Eastman Fine Chemical of Kingsport, Tenn.) was added to Tubes 5 and 6. For Example 14, 1.0 mg HPMCP(NF grade from Eastman Chemical Company) was added to Tubes 7 and 8.

Dissolution performance was measured at 37° C. using the microcentrifuge method described in Example 1. For each test, 0.616 mg of Drug 3 was added to the microcentrifuge tube. At time 0, 1.8 mL PBS was added to each of the tubes. Drug concentration was measured using HPLC, with a mobile phase of 60 vol. % 0.02 M $KH_2PO_4$, pH 3.0 in ACN, and diode array detection at 254 nm. Results of the dissolution tests are shown in Table 5.1.

TABLE 5.1

| | [Drug 3] (μg/mL) | | | |
|---|---|---|---|---|
| Time (mins) | Control 5 (Drug 3 only) | Example 12 (1:2 Drug 3:CAT) | Example 13 (1:2 Drug 3:CAP) | Example 14 (1:2 Drug 3:HPMCP) |
| 10 | 3 | 23 | 18 | 22 |
| 20 | 11 | 23 | 21 | 18 |
| 40 | 6 | 11 | 22 | 6 |
| 90 | 7 | 6 | 25 | 6 |
| 180 | 1 | 5 | 23 | 12 |

Table 5.2 reports $C_{max}$, $AUC_{180}$ and theoretical $C_{max}$. The $C_{max}$ of Examples 12-14 were 2.0-fold to 2.3-fold that of Control 5, while the $AUC_{180}$ for Examples 12-13 were 1.6-fold to 4.0-fold that of Control 5.

TABLE 5.2

| Example | $C_{max}$ (μg/mL) | $AUC_{180}$ (min*μg/mL) | Theoretical $C_{max}$ (μg/mL) |
|---|---|---|---|
| Control 5 (Drug 3 only) | 11 | 1000 | 342 |
| 12 (1:2 Drug 3:CAT) | 23 | 1600 | 342 |
| 13 (1:2 Drug 3:CAP) | 25 | 4000 | 342 |
| 14 (1:2 Drug 3:HPMCP) | 22 | 1600 | 342 |

EXAMPLES 15-16

These examples demonstrate compositions of a drug in a high-energy crystalline state (here the solubility-improved form) and a concentration-enhancing polymer. The mesylate salt of the epidermal growth factor receptor tyrosine kinase inhibitor (EGFR-TK inhibitor) [6,7-Bis(2-methoxy-ethoxy)-quinazolin-4-yl]-(3-ethynyl-phenyl)amine (Drug 4) has been isolated in various polymorphs with different solubilities. The "A" form, for example, has a solubility of 102 μgA/mL in water, while the "C" form has a solubility of 28 μA/mL. These polymorphs are metastable forms that can interconvert rapidly with more stable forms to reach a lower equilibrium concentration in the environment of use. In these examples, the "A" polymorph was studied.

For these tests, 2.5 mg of polymorph "A" of Drug 4 was added to each of 6 microcentrifuge tubes. For Control 6, no concentration-enhancing polymer was added to Tubes 1 and 2. For Example 15, 1.2 mg of HPMCAS-MF was added to Tubes 3 and 4. For Example 16, 1.2 mg of HPMCP was added to tubes 5 and 6.

Dissolution performance was measured at 37° C. using the microcentrifuge method. At time 0, 1.8 mL PBS was added to tubes 1 to 6. Drug concentration was measured using HPLC. The mobile phase was a 55/45 (v/v) mixture of 0.2 wt % trifluoroacetic acid adjusted to pH 3.0 with ammonium hydroxide in HPLC water and 85/15 (v/v) acetronitrile/iso-propyl alcohol. The analytical column used was an Inertsil C8, and the drug concentration was determined using diode array detection at 252 nm. Results of the dissolution tests are shown in Table 6.1.

TABLE 6.1

| | [Drug 4] (μg/mL) | | |
|---|---|---|---|
| Time (mins) | Control 6 (Drug 4 only) | Example 15 2.1:1 (Drug 4:HPMCAS-MF) | Example 16 2.1:1 (Drug 4:HPMCP) |
| 4 | 11 | 287 | 164 |
| 10 | 18 | 113 | 41 |
| 20 | 21 | 34 | 32 |
| 40 | 14 | 36 | 44 |
| 90 | 18 | 29 | 49 |
| 1200 | 10 | 32 | 121 |

Table 6.2 shows the $C_{max}$ for the composition containing HPMCAS-MF (Example 15) was 13.7-fold that of Control 6, while the $AUC_{90}$ was 3.2-fold that of Control 6. The $C_{max}$ for the composition containing HPMCP (Example 16) was 7.8-fold that of Control 6, while the $AUC_{90}$ was 2.9-fold that of Control 6.

TABLE 6.2

| Example | $C_{max}$ (μg/mL) | $AUC_{90}$ (min*μg/mL) | $C_{1200}$ (μg/mL) | Theoretical $C_{max}$ (μg/mL) |
|---|---|---|---|---|
| Control 6 (Drug 4 only) | 21 | 1500 | 10 | 1391 |
| 15 (2.1:1 Drug 4:HPMCAS-MF) | 287 | 4800 | 32 | 1391 |
| 16 (2.1:1 Drug 4:HPMCP) | 164 | 4400 | 121 | 1391 |

EXAMPLE 17

This example demonstrates a solubilizing agent mixed with the drug as the solubility-improved form of the drug. The solubility of sertraline HCl (Drug 5) at 37° C. was determined at pH 3.1 in water (adjusted to pH 3.1 with acetic acid) and in saturated citric acid at the same pH. As shown in Table 7.1, the solubility of Drug 5 was dramatically increased in the presence of citric acid, giving a solubility-improvement factor of 9.3. Thus, citric acid is an excellent solubilizing agent for Drug 5.

TABLE 7.1

| Drug Form | Sertraline HCl (mg/mL) |
|---|---|
| Drug 5 | 3 |
| Drug 5 in saturated citric acid | 28 |

For Example 17, a solution was prepared containing 1,000 μg/mL Drug 5, 500 μg/mL citric acid, and 1,000 μg/mL HPMCAS-MF in phosphate buffer (pH 7.9). For Control 7, solution containing no concentration-enhancing polymer was prepared.

Dissolution performance was measured at 37° C. using the microcentrifuge method described in Example 1. Samples were taken at 15, 30, 60, 120, and 240 minutes as described in Example 1 and analyzed for Drug 5 using the same procedure described in Example 10. The results of these tests are shown in Table 7.2, with various calculated values reported in Table 7.3.

TABLE 7.2

| Example | Time (min) | [Drug 5] (μg/mL) |
|---|---|---|
| 17 | 15 | 106 |
|  | 30 | 94 |
|  | 60 | 55 |
|  | 120 | 59 |
|  | 240 | 58 |
| Control 7 | 5 | — |
|  | 15 | 64 |
|  | 30 | 52 |
|  | 60 | 55 |
|  | 120 | 52 |
|  | 240 | 39 |

TABLE 7.3

| Example | $C_{max}$ (μg/mL) | $AUC_{120}$ (min*μg/mL) | Theoretical $C_{max}$ (μg/mL) |
|---|---|---|---|
| Example 17 | 106 | 8700 | 1000 |
| Control 7 | 64 | 6500 | 1000 |

These data show that the addition of the concentration-enhancing polymer HPMCAS resulted in a $C_{max}$ for Example 17 that was 1.7-fold that of Control 7. In addition, the $AUC_{120}$ was 1.3-fold than that of Control 7.

EXAMPLE 18

This example demonstrates the use of the present invention in vivo. Aqueous solutions of a soluble drug form and a concentration-enhancing polymer were administered to dogs. The solubility-improved drug form was the mesylate salt of the drug 4-[3-[4-(2-methylimidazol-1-yl)phenylthio]phenyl]-3,4,5,6-tetrahydro-2H-pyran-4-carboxamide hemifumarate (Drug 6). For this drug, the solubility of the hydrochloride salt is 0.37 mgA/mL at pH 4, while the solubility of the mesylate salt (the solubility-improved form of the drug) is 3.7 mgA/mL at pH 4. The solubility of both of these drug forms decreases with increasing pH. At pH 7, the solubility of the hydrochloride salt is 0.0009 mgA/mL, and the solubility of the mesylate salt is 0.0042 mgA/mL. Ideally, it would be useful to maintain the higher solubility of the solubility-improved drug form in gastric fluid, and also to maintain the drug concentration as the pH increases in intestinal solution.

Example 18 was prepared as a suspension containing 15 mgA Drug 6 in a 1:10 (w/w) Drug 6/HPMCAS-LF physical mixture. Control 8 contained no HPMCAS. The suspension compositions for Example 18 and Control 8 are presented in Table 8.1.

TABLE 8.1

| Component | Example 18 (g) | Control 8 (g) |
|---|---|---|
| Drug 6 (0.814 potency) | 0.246 | 0.246 |
| HPMCAS | 2.000 | — |
| Sterile water | 40 | 40 |
| pH | 2.9 | 4.1 |

After an overnight fast, dogs were dosed with 20 mL of the suspension, followed immediately by a 10 cc flush of air via a surgically-placed access port, directly into the ascending colon. Blood (5 mL) was collected from the jugular vein pre-dosing and at hours 0.25, 0.5, 1, 2, 4, 6, 8, 12 and 24 post-dosing.

Plasma concentrations of Drug 6 in standards, controls and study samples were determined by LC/MS analysis. Aliquots of 100 μL of plasma from samples, standards and controls were added into the appropriate wells of a 96-well plate followed by addition of 5 μL of internal standard (IS), 4-[(5-Fluoro-3-[4-(2-methylimidazol-1-yl)benzyloxy]phenyl]-3, 4,5,6-tetrahydro-2H-pyran-4-carboxamide (10 μg/mL in 50/50 acetonitrile/water) into each well; followed by the addition of 100 μL acetonitrile into each well. After vortexing and centrifugation (5 minutes at 1730 G), the supernatant of each well was transferred to a new well of a 96-well plate and 20 μL was injected onto a LC/MS system. The reverse-phase HPLC system consisted of a Waters C18 Symmetry® analytical column (2.1 mm×150 mm). The mobile phase solvents were: solvent A=5 mM ammonium acetate, with 1% isopropyl alcohol per liter of mobile phase and solvent B=acetonitrile, with 1% isopropyl alcohol per liter of mobile phase. The gradient was 0-3.0 minutes, 100% A to 0% A, at 3.1 minute switch back to 100% A, at a flow rate of 0.5 mL/min. Retention times for Drug 6 and IS were both approximately 2.6 minutes. Detection was accomplished by a SCIEX PE API-150 mass spectrometer equipped with a Turbo IonSpray interface. The positive ions were monitored for the quantification of Drug 6 (m/z 394.1) and IS (m/z 410.3), respectively. The ratio of peak area responses of Drug 6 relative to the internal standard was used to construct a standard curve using a linear least square regression with a 1/x2 weighting. The lower limit of quantification (LLOQ) and upper limit of quantification (ULOQ) of the plasma assay were 0.01 and 5 μg/mL, respectively. The performance of the assay was monitored by the inclusion of quality control samples prepared in dog plasma.

Pharmacokinetic data are presented in Table 8.2, where $C_{max}$ is the maximum observed plasma Drug 6 concentration, averaged over the number of dogs dosed with each form. $AUC_{1200}$ is the average area under the plasma Drug 6 concentration vs. time curve from 0 to 24 hours (1200 minutes).

TABLE 8.2

| Example | Dose[1] (mg) | n[2] | $C_{max}$ (μg/mL) | $AUC_{1200}$ (μg-hr/mL) |
|---|---|---|---|---|
| Example 18 | 50 | 1 | 1.41 | 9.63 |
| Control 8 | 50 | 2 | 0.28 | 3.12 |

[1]The average weight of the dogs used in this study was around 9 kg
[2]Number of dogs studied These data demonstrate that the physical mixture of HPMCAS and Drug 6, when colonically dosed to a beagle dog, gave a higher systemic Drug 6 exposure than that obtained by dosing the Drug 6 alone. The $C_{max}$ and $AUC_{1200}$ for the HPMCAS form was 5.0-fold and 3.1-fold that of the control, respectively. These data demonstrate the utility of the invention in delivery of compounds to the colon.

EXAMPLE 19

Example 19 demonstrates a composition similar to that used in Example 18 that was also tested in vitro as follows. Example 19 was prepared by first adding 20 mL deionized water to a small glass beaker, and adjusting the pH to between pH 1 and 2, with 10 M HCl. Next, 100 mg of Drug 6 was dissolved in this solution by stirring for 5 minutes. During this time the pH remained in the range of 1-2, resulting in a final Drug 6 concentration of 5 mg/mL.

This mixture of Drug 6 was then equally divided into two small glass beakers, each containing a magnetic stir bar. A 10 mg sample of HPMCAS-LF was added to one beaker (Example 19) and no concentration-enhancing polymer was added to the second beaker (Control 9).

Thus, the drug/polymer ratio in this test was 1:4 (wt:wt). The pH of both was then adjusted to pH 6.8 using 0.1 M and 0.01 M NaOH. The beakers were covered and the mixtures stirred.

Samples (≈1 mL) were taken at 60, 120, 180, 240 and 1440 minutes using a glass Pasteur pipette. Each sample was transferred into a 1.0 mL plastic syringe with a Gelman Acrodisc 1.2 μm syringe filter attached. The sample was then expelled through the filter into a glass HPLC injection vial, capped, immediately assayed by HPLC, and compound concentration calculated. Samples were analyzed using a Zorbax C8 Reverse Phase, 5 μm, 4.6×150 mm column with detection at 264 nm.

The results of these tests are given in Tables 9.1 and 9.2. They show that the C of Example 19 was 2.5-fold that of Control 9. In addition, the $AUC_{180}$ for Example 19 was 3.7-fold that of Control 9. These data agree well with the in vivo tests described in Example 18.

TABLE 9.1

| | [Drug 6] (μg/mL) | |
|---|---|---|
| Time (min) | Example 19 (1:4 Drug 6:HPMCAS-LF) | Control 9 (Drug 6 only) |
| 60 | 46 | 21 |
| 120 | 52 | 7 |
| 180 | 47 | 9 |
| 240 | 51 | 6 |
| 1440 | 36 | 4 |

TABLE 9.2

| Sample | $C_{max}$ (μg/mL) | $AUC_{180}$ (min*μg/mL) | Theoretical $C_{max}$ (μg/mL) |
|---|---|---|---|
| Example 19 (1:4 Drug 6:HPMCAS-LF) | 52 | 7290 | 250 |
| Control 9 (Drug 6 only) | 21 | 1950 | 250 |

EXAMPLE 20

The formation of polymer/drug aggregates in solution was demonstrated using dynamic light-scattering analysis. Varying amounts of amorphous Drug 1 and HPMCAS-MF were added to PBS, and light-scattering was measured using a PSS-NICOMP 380 Submicron Particle Sizer. For these experiments, 0.1, 1.0, 10.0, 25.0, or 50.0 mg of solid amorphous Drug 1 was added to a mortar with 200 mg of HPMCAS-MF, and mixed using a spatula. Each drug/polymer mixture was then added to 50 mL PBS equilibrated to 37° C. for two hours. Table 10 shows the final polymer and drug concentrations present in the solution. After 2 hours, 1 mL of solution was removed and centrifuged at 13,000 rpm for five minutes. Dynamic light-scattering (based on diffusion of particles) of the supernatant of each of the centrifuged solutions was measured, and the size of any drug and polymer particles in the solution was calculated. Concentrations of drug and polymer in solution, and the corresponding average particle size for the bulk of particles in solution are shown in Table 10. It should be noted for solutions No. 5 and No. 6, the value reported is an average with approximately 85% of the particle volume being within about 30% of this average size.

TABLE 10

| Solution No. | Drug 1 Concentration (mg/mL) | HPMCAS-MF Concentration (mg/mL) | Particle Size (nm) |
|---|---|---|---|
| 1 | 0 | 2.0 | 12 |
| 2 | 0.002 | 2.0 | 18 |
| 3 | 0.02 | 2.0 | 16 |
| 4 | 0.2 | 2.0 | 14 |
| 5 | 0.5 | 2.0 | 84 |
| 6 | 1.0 | 2.0 | 83 |

When no drug is present (solution No. 1), small particles about 10 to 20 nm in size are present due to aggregation of the polymer (HPMCAS-MF), likely as a result of its amphiphilicity. At low concentrations of amorphous Drug 1 (0.002 to 0.2 mg/mL), light-scattering shows only small particles in solution (about 10 to 20 nm in size), as are present for polymer alone. For higher concentrations of amorphous Drug 1 (≧0.5 mg/mL), which are above the solubility of amorphous Drug 1 (approximately 0.2 to 0.4 mg/mL) particles are present with an average size of about 80 to 85 nm. This demonstrates the formation of polymer/drug aggregates in solution, and shows that the amount of drug required for aggregate formation is approximately equal to or greater than the amorphous drug solubility.

The concentration-enhancement provided by these polymer/drug aggregates was demonstrated for Drug 1 concentrations higher than those shown in Table 10 (much greater than the amorphous drug solubility). For the dissolution test described in Example 9, 10.0 mg/mL amorphous Drug 1 was added to PBS at 37° C., with 20 mg/mL HPMCAS-MF. The control for Example 9 was amorphous drug alone. Drug 1 concentrations measured at 1.5 hours showed 224 μg/mL for amorphous drug alone, and 8,099 μg/mL for Example 9. The ratio of drug to polymer for Example 9 corresponds to the ratio used in solution No. 6 above (Table 10). The formation of drug/polymer aggregates in solution allowed Drug 1 to remain in solution at a concentration far in excess of its amorphous solubility.

To determine the drug/polymer aggregate compositions, solutions No. 4, No. 5, and No. 6 above (Table 10) were made again and analyzed using HPLC and NMR. Drug and polymer were added to PBS at 37° C. Two hours after the addition of drug and polymer samples were centrifuged (13,000 rpm for 5 minutes). The concentrations of free drug and free polymer in the supernatant were determined by NMR. HPLC was used to determine the total amount of dissolved drug in the supernatant following centrifugation which consists of "free" (solvated) drug and drug in polymer/drug aggregates. The centrifuged precipitate was dissolved in DMSO and analyzed by NMR to obtain the concentrations of drug and polymer. The amount of drug contained in the drug/polymer aggregates was found by subtracting the concentration of free drug in the supernatant from the total dissolved drug. The amount of polymer contained in the drug/polymer aggregates was found by subtracting the free polymer and the polymer in the precipitate from the total polymer dosed. The results are shown in Table 11 below.

TABLE 11

| Solution (No.) | Total Drug 1 Conc. (μg/mL) | HPMCAS-MF Conc. (μg/mL) | Free Drug 1 Conc. In Solution (μg/mL) | Free Polymer Conc. In Solution (μg/mL) | Total Dissolved Drug 1 (μg/mL) | Drug 1 in Precipitate (μg/mL) | Polymer in Precipitate (μg/mL) | Drug 1 in Aggregates (μg/mL) | Polymer in Aggregates (μg/mL) |
|---|---|---|---|---|---|---|---|---|---|
| 4 | 200 | 2000 | 166 | 1770 | 198 | 0 | 0 | 32 | 230 |
| 5 | 500 | 2000 | 265 | 1367 | 462 | 47 | 88 | 197 | 545 |
| 6 | 1000 | 2000 | 301 | 1004 | 542 | 377 | 535 | 241 | 461 |

The data in Table 11 show that for drug concentrations exceeding the solubility limit (solutions No. 5 and No. 6), a large percentage of the total soluble drug is contained in drug-polymer aggregates. In addition, the free drug concentration for solution No. 6 is about 3.8-fold the solubility of the crystalline Drug 1 (80 μg/mL) and about 1.5-fold the solubility of amorphous Drug 1 (200 μg/mL).

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A composition comprising:
   (a) a drug in a pharmaceutically acceptable solubility-improved form that is a crystalline highly soluble salt form other than the crystalline hydrochloride salt; and
   (b) a concentration-enhancing polymer selected from the group consisting of hydroxypropyl methyl cellulose acetate, hydroxypropyl methyl cellulose, hydroxypropyl cellulose, methyl cellulose, hydroxyethyl methyl cellulose, hydroxyethyl cellulose acetate, hydroxyethyl ethyl cellulose, and mixtures thereof
   wherein
   said drug alone has an aqueous solubility of up to 2 mg/mL at pH 1 to 8,
   said composition is not a dispersion and said drug and said polymer are present as particles in a dry physical mixture.

2. A composition comprising:
   (a) a drug in a pharmaceutically acceptable solubility-improved form that is a crystalline highly soluble salt form other than the crystalline hydrochloride salt; and
   (b) carboxymethyl ethyl cellulose
   wherein
   said drug alone has an aqueous solubility of up to 2 mg/mL at pH 1 to 8,
   said composition is not a dispersion and said drug and said polymer are present as particles in a dry physical mixture.

3. A composition comprising:
   (a) a drug in a pharmaceutically acceptable solubility-improved form that is a crystalline highly soluble salt form other than the crystalline hydrochloride salt; and
   (b) a concentration-enhancing polymer selected from acrylate and methacrylate copolymers
   wherein
   said drug alone has an aqueous solubility of up to 2 mg/mL at pH 1 to 8,
   said composition is not a dispersion and said drug and said polymer are present as particles in a dry physical mixture.

4. The composition of any of claims 1-3 wherein said crystalline highly soluble salt form is selected from the group consisting of bromide, acetate, iodide, mesylate, phosphate, maleate, citrate, sulfate, tartrate, and lactate salts.

5. The composition of any of claims 1-3 wherein said crystalline highly soluble salt form is selected from the group consisting of sodium, calcium, potassium, zinc, magnesium, lithium, aluminum, meglumine, diethanolamine, benzathine, choline, and procaine salts.

6. The composition of any of claims 1-3 wherein said drug alone has an aqueous solubility of less than 0.01 mg/mL at pH 1 to 8.

7. The composition of any of claims 1-3 wherein said drug is selected from antihypertensives, antianxiety agents, anti-clotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-parkinsonism agents, anti-Alzheimer's disease agents, antibiotics, anti-depressants, and antiviral agents.

* * * * *